United States Patent [19]

Osten et al.

[11] Patent Number: 5,729,333

[45] Date of Patent: *Mar. 17, 1998

[54] CHARACTERIZING BIOLOGICAL MATTER IN A DYNAMIC CONDITION USING NEAR INFRARED SPECTROSCOPY SPECTRUM

[75] Inventors: David W. Osten; Hatim M. Carim, both of St. Paul, Minn.; James B. Callis, Seattle, Wash.

[73] Assignees: Minnesota Mining and Manufacturing Company, St. Paul, Minn.; The Board of Regents of The University of Washington, Seattle, Wash.

[*] Notice: The portion of the term of this patent subsequent to Dec. 22, 2012, has been disclaimed.

[21] Appl. No.: 995,951

[22] Filed: Dec. 22, 1992

Related U.S. Application Data

[63] Continuation of Ser. No. 408,890, Sep. 18, 1989, abandoned.
[51] Int. Cl.$^6$ .......................................... A61J 1/05
[52] U.S. Cl. ................................................ 356/39
[58] Field of Search .......................... 364/413.08, 498; 128/633, 664; 356/39–42; 250/338.1, 338.5, 339–341

[56] References Cited

U.S. PATENT DOCUMENTS

| | | | |
|---|---|---|---|
| 3,648,160 | 3/1972 | Beaver | 324/30 B |
| 3,877,818 | 4/1975 | Button et al. | 356/186 |
| 4,017,192 | 4/1977 | Rosenthal | 356/39 X |

(List continued on next page.)

FOREIGN PATENT DOCUMENTS

| | | | |
|---|---|---|---|
| 0240742 | 6/1987 | European Pat. Off. | G01N 33/49 |
| WO 90/04353 | 5/1990 | WIPO . | |
| WO 90/04941 | 5/1990 | WIPO . | |

OTHER PUBLICATIONS

Stark, E., and Luchter, K., "Near–Infrared Analysis (NIRA): A Technology for Quantitative and Qualitative Analysis," *Applied Spectroscopy Reviews*, 22(4):335–399 (1986).

(List continued on next page.)

*Primary Examiner*—Gail O. Hayes
*Assistant Examiner*—Junghoon Kenneth Oh
*Attorney, Agent, or Firm*—Gary L. Griswold; Walter N. Kirn; John H. Hornickel

[57] ABSTRACT

A method is provided for predicting a property of a matter of biological origin, such as biological fluid, containing water, in a dynamic condition where the biological fluid may be approximated to contain two compartments where one compartment has a proportionally larger or smaller amount of water than the other compartment having the property of interest. The method involves establishing a training set in the near-infrared (NIR) region with independent quantification of the property of the fluid using known techniques. The training set is mathematically analyzed according to a correlation developed by regression analysis after employment of a pre-processing technique such as a multiple derivative transformation of spectra or a ratioing of two wavelengths in the spectra. The result is a mathematical transformation equation which quantitatively relates spectral intensities at specific wavelengths to the property of interest. This transformation equation may be applied to unknown samples so as to predict their properties, thereby eliminating need for the reference method except for validation or recalibration. The method provides rapid and accurate prediction of the property of the unknown sample, which may be the property of hematocrit or hemoglobin concentration in whole animal blood. Other analyses of properties in the biological fluid such as oxygen saturation in hemoglobin in whole animal blood may be included in the mathematical analysis to further refine the prediction of the property of interest. Also, a loop from the patient is disclosed for the purpose of monitoring the property of interest nearly simultaneously with changes in that property of interest.

70 Claims, 14 Drawing Sheets

U.S. PATENT DOCUMENTS

| | | | |
|---|---|---|---|
| 4,086,915 | 5/1978 | Kofsky et al. | 128/2 L |
| 4,114,604 | 9/1978 | Shaw et al. | 128/2 L |
| 4,210,809 | 7/1980 | Pelavin | 250/343 |
| 4,223,680 | 9/1980 | Jöbsis | 128/633 |
| 4,243,883 | 1/1981 | Schwarzmann | 250/343 |
| 4,281,645 | 8/1981 | Jöbsis | 128/633 |
| 4,303,336 | 12/1981 | Cullis | 356/39 |
| 4,345,150 | 8/1982 | Tamura et al. | 250/339 |
| 4,407,290 | 10/1983 | Wilber | 128/633 |
| 4,427,889 | 1/1984 | Müller | 250/339 |
| 4,447,150 | 5/1984 | Heinemann | 356/41 |
| 4,466,076 | 8/1984 | Rosenthal | 364/571 |
| 4,485,820 | 12/1984 | Flower | 128/633 |
| 4,523,279 | 6/1985 | Sperinde et al. | 364/416 |
| 4,586,513 | 5/1986 | Hamaguri | 128/633 |
| 4,633,087 | 12/1986 | Rosenthal et al. | 250/341 |
| 4,642,778 | 2/1987 | Hieftje et al. | 364/498 |
| 4,651,741 | 3/1987 | Passafaro | 128/633 |
| 4,655,225 | 4/1987 | Dahne et al. | 128/633 |
| 4,660,151 | 4/1987 | Chipman et al. | 364/498 |
| 4,701,838 | 10/1987 | Swinkels et al. | 364/164 |
| 4,745,279 | 5/1988 | Karkar et al. | 250/343 |
| 4,800,279 | 1/1989 | Hieftje et al. | 250/339 |
| 4,805,623 | 2/1989 | Jöbsis | 128/633 |
| 4,825,076 | 4/1989 | Shields | 250/343 |
| 4,972,331 | 11/1990 | Chance | 364/550 |
| 4,975,581 | 12/1990 | Robinson et al. | 250/339 |

OTHER PUBLICATIONS

Ciurczak, E.W., "Uses of Near–Infrared Spectroscopy in Pharmaceutical Analysis," *Applied Spectroscopy Reviews*, 23(1&2):147–163 (1987).

Wetzel, D.L., "Near–Infrared Reflectance Analysis: Sleeper Among Spectroscopic Techniques," *Analytical Chemistry*, 55(12):1165–1176 (Oct. 1983).

Wyatt, J.S., Delpy, D.T., Cope, M., Wray, S., and Reynolds, E.O.R., "Quantification of Cerebral Oxygenation and Haemodynamics in Sick Newborn Infants by Near Infrared Spectrophotometry," *The Lancet*, 1063–1066 (Nov. 8, 1986).

Osborne, B.G., and Fearn, T., "Technical Note–Discriminant Analysis of Black Tea By Near Infrared Reflectance Spectroscopy," *Food Chemistry*, 29:233–238 (1988).

Lum et al., "Evaluation of Pulse Oximetry With EKG Synchronization," IEEE Engineering in Medicine & Biology Society 10th Annual International Conference, Copyright 1988.

Lee et al., "Measurement of Percent Carboxyhemoglobin With Pulse–Oximetry Technique," IEEE Engineering in Medicine & Biology Society 10th Annual International Conference, Copyright 1988.

Dickensheets et al., "Pathlength Independent Spectrophotometric Measurement of Hemoglobin in Solution," IEEE Engineering in Medicine & Biology Society 11th Annual International Conference, published Nov. 1989.

Lee et al., "Simultaneous Measurement of Percent Carboxyhemoglobin and Functional Oxygen Saturation," IEEE Engineering in Medicine & Biology Society 11th Annual International Conference, published Nov. 1989.

Dickensheets, "A Study of Non–Invasive Quantitative Estimation of Circulating Bilirubin in Newborns," Masters Thesis University of Washington, Chapters II-V, published Mar. 3, 1989.

Chance et al., "Time–Resolved Spectroscopy of Hemoglobin and Myoglobin in Resting and Ischemic Muscle", *Analytical Biochemistry* 174, pp. 698–707 (1988).

Barlow et al., "Absorption Measurements for Oxygenated and Reduced Hemoglobin in the Range 0.6–1.88 Microns", *Clinical Chemistry*, vol. 8, No. 1 (1962).

H. Martens et al., "Multivariate calibration", *TRAC: Trends in Analytical Chemistry*, vol. 3, No. 8, pp. 204–210, Sep. 1, 1984.

M. Josefson et al., "Optical Fiber Spectrometry", *Analytical Chemistry*, vol. 60, No. 24, pp. 2666–2671, Dec. 15, 1988.

A. Van Toorenenbergen et al., "Measurement of Total Serum Protein", *Journal of Clinical Chemistry & Clinical Biochemistry*, vol. 26, No. 4, pp. 290–211, Jul. 1, 1988.

R. Looder et al., "Assessment of the Feasibility of Determination of Blood Constituents", *Talanta*, vol. 36, No. 1, pp. 193–198, Mar. 1, 1989.

E. Peuchant et al., "Determination of Serum Cholesterol", *Analytical Chemistry*, vol. 59, No. 14, pp. 1816–1819, Jul. 15, 1987.

P. Robert et al., "Multivariate Analysis", *Analytical Chemistry*, vol. 59, No. 17, pp. 2187–2191, Sep. 1, 1987.

M. Nyden et al., "Spectroscopic Quantitative Analysis", *Applied Spectroscopy*, vol. 42, No. 4, pp. 588–594, Apr. 1, 1988.

H. Kisner et al., "Multiple Analytical Frequencies and Standards", *Analytical Chemistry*, vol. 55, No. 11, pp. 1703–1707, Sep. 1, 1983.

P. Geladi et al., "Linearization and Scatter Correction for Near Infrared", *Applied Spectroscopy*, vol. 39, No. 3, pp. 491–500, Jul. 1, 1985.

G. Janatsch et al., "Multivariate Calibration for Assays in Clinical Chemistry", *Analytical Chemistry*, vol. 61, No. 18, pp. 2016–2023, Sep. 15, 1989.

"Pathlength Independent Spectrophotometric Measurement of Hemoglobin in Solution", *IEEE Engineering in Medicine and Biology Society*, Dickensheets et al., Nov. 8, 1989, pp. 1090–1991.

"Simultaneous Measurement of Percent Carboxyhemoglobin and Functional Oxygen Saturation", *IEEE Engineering in Medicine and Biology Society*, Lee et al., Nov. 8, 1989, pp. 1092–1093.

"Noninvasive Determination of Hemoglobin Saturation in Dogs by Derivative Near–infrared Spectroscopy", *American Physiological Society*, Ferrari et al., 1989, pp. H1493–H1499.

"Reflectance Measurements of Hematocrit and Oxyhemoglobin Saturation", *American Physiology Society*, Steinke et al., Jul., 1987, pp. H147–H153.

"Review: Infrared Spectrometry", *Anal. Chem.*, (McDonald), 1986, pp. 1906–1925.

"Focus Near–Infrared Spectrometry in Clinical Analysis", *Anal. Chem.*, Anon., Jul., 1986, pp. 874, 876.

"A Comparative Study of Two Computerized Spectrophotometers for the Near–Infrared Analysis of Wheat for Protein", *Applied Spectroscopy*, 1986, Williams et al., pp. 785–790.

"Salinity Determination Using NIRA", Hirschfeld, *Appl. Spectrosc.* 1985, 39(4), 7400–741.

"Near Infrared Analysis", *Analytical Instrumentation*, Honigs, 1985, pp. 1–62.

"Near–Infrared Determination of Several Physical Properties of Hydrocarbons", *Anal. Chem.*, vol. 57, No. 2, Honigs et al., Feb., 1985, pp. 443–445.

"A New Method for Obtaining Individual Component Spectra from Those of Complex Mixtures", *Appl. Spectroscopy*, vol. 38, No. 3, Honigs et al., 1984, pp. 317–322.

"Multicomponent Quantitative Analysis", *Appl. Spectroscopy Reviews*, Brown and Obremski, 1984, pp. 373–418.

"Predicting Forage Quality by Infrared Reflectance Spectroscopy", *Journal of Animal Science*, vol. 43, No. 14, Norris et al., 1976, pp. 889–897.

"Compscan Systems Operator's Manual, vol. I—Instruction Manual", Pacific Scientific Company, Caseiero et al., 1985, pp. 6–12, 29–185.

5,729,333

CHARACTERIZING BIOLOGICAL MATTER IN A DYNAMIC CONDITION USING NEAR INFRARED SPECTROSCOPY SPECTRUM

This is a continuation of application Ser. No. 07/408,890 filed Sep. 18, 1989 now abandoned.

FIELD OF THE INVENTION

The present invention relates to the analysis of a sample of matter of biological origin in a dynamic condition using the near-infrared (NIR) spectrum of that biological matter having a water content. The method permits prediction of a property of interest because the biological matter may be approximated to contain two compartments where one compartment has a proportionally larger or smaller amount of water than the other compartment having the property of interest. Analysis of an unknown sample in a dynamic condition is achieved by use of mathematical techniques developed using a NIR spectral training set of known samples and independent quantification of the property of interest in the known samples in that training set.

BACKGROUND OF THE INVENTION

Presence of water in an organism is the common denominator of life. The corpus of an organism is compartmentalized with each compartment capable of being distinguished by the amount of water it contains. The processes of osmosis and reverse osmosis in an organism act to stabilize this compartmentalization.

Determination of the volume fraction or percentage concentration of components other than water in the various compartments of biological matter, such as tissue or blood, is often critical to the determination of the well-being or homeostasis of the organism. Whether in the botanical, medical, zoological or veterinary arts, because the circulation of biological fluid or existence of certain biological tissue in an organism is necessary for life, the diagnosis of such biological matter provides an excellent medium to assess the homeostatic condition of the organism.

Blood of animals circulates essential nutrients of life. Erythrocytes, red blood cells, flowing in the blood plasma carry oxygen to all other cells of the organism. Hematocrit is the volume fraction of agglomerated erythrocytes in whole blood. Hemoglobin is the chemical molecule in the erythrocytes which transports oxygen to the cells. Hemoglobin may take several forms depending on the presence or absence of oxygen or other chemicals which may be bonded to active sites in the hemoglobin molecule. Hematocrit in whole blood has been found to have a suitable direct mathematical correlation to the concentration of hemoglobin, providing the blood has few or no lysed erythrocytes.

Water is omnipresent in whole blood. Hemoglobin is dissolved in the erythrocytes, while plasma is principally water. But the amount of water in which hemoglobin is dissolved, and hence in erythroctyes, is comparatively less than the amount of water in the plasma.

Clinical analysis of an organism requires monitoring of the status of or the changes in condition. As a result of injury or illness or other deleterious biological conditions, the hematocrit or the concentration of hemoglobin in erythrocytes available for oxygen transport to the cells of the organism may be diminished below healthy levels even to the point of critical life sustaining levels. Also, analysis of various types of anemia is vital to continuing successful treatment of a patient, especially in critical care facilities such as emergency rooms, operating rooms, or intensive care units, including neo-natal units. Less traumatic but just as vital, most blood donors must undergo hematocrit testing to assure that their blood to be donated has appropriate hemoglobin levels for later use.

Several types of techniques have been known for the analysis of blood during patient care. Hemoglobin concentrations are measured traditionally using lengthy and complicated procedures which require the preconditioning, i.e., chemical modification or component separation, of a blood sample withdrawn from the body. The traditional methods destroy the blood, preventing its return to the body.

One popular method for the determination of hemoglobin involves (1) lysing the red blood cells by hypotonic shock or sonification, (2) removal of the red blood cell membranes to produce a clear solution, (3) addition of a cyanide ion reagent to normalize or convert the various forms of hemoglobin to a single form hemoglobin (e.g., cyanomet hemoglobin), and (4) spectrophotometric analysis to derive the hemoglobin concentration of the normalized sample.

Because of the complicated chemical procedure for determination of hemoglobin concentration, and because of the known direct correlation between hematocrit and hemoglobin concentration, methods for independently determining hematocrit have been developed.

The most common methods for measurement of hematocrit can be divided into two categories: centrifugal attribution in a test tube of specific diameter and Coulter counting.

Centrifugal attribution involves centrifuging of blood withdrawn from the body in a tube of specific diameter at pre-selected centrifugal forces and times that serve to separate the blood into two portions. The heavier portion is the agglomeration of erythrocytes in the whole blood. The lighter portion is plasma dominated by water. The ratio of the volume of the erthrocytes to the total volume of the blood sample in the centrifuge tube is the hematocrit.

Coulter counting determines hematocrit by physical counting of red blood cells and a determination, through the size of each cell on a cell-by-cell basis, the volume of each. After a predetermined number of blood cells are counted, the hematocrit is determined by the number of red blood cells counted multiplied by the mean volume of the blood cells for a given blood sample.

As may be understood by considering such current methods, considerable manipulation and laboratory analysis is necessary for each individual blood sample drawn from the body of the patient. Whether measuring hematocrit or hemoglobin concentration, the blood sample is withdrawn from the patient and inevitably taken from the immediate vicinity of the patient for analysis using expensive, stationary instrumentations that require preconditioning of the sample in order to analyze it.

Efforts to spectrally analyze blood samples for hematocrit or hemoglobin concentration have been attempted. U.S. Pat. No. 4,243,883 describes a monitor of a flowing stream of blood using a discrete near-infrared wavelength. U.S. Pat. No. 4,745,279 describes a dual path NIR spectral analysis at discrete wavelengths of flowing whole blood. U.S. Pat. No. 4,805,623 describes a NIR spectral method and apparatus using multiple wavelengths to determine the concentration of a dilute component of known identity in comparison with a reference component of known concentration.

The near-infrared (NIR) spectral region of electromagnetic radiation, from about 680 nanometers to 2700 nanometers, contains absorbance peaks for the various forms of hemoglobin and water. Prior spectral analytical efforts have focused on the measurement of the diffuse transmission or reflectance of near infrared light through blood samples. However, light scattering in the samples and other properties which interfere with accurate measurement cause variances in the specific spectrum taken. As a result, even using measurements taken with sensitive instrumentation is not satisfactory. Moreover, the choice of specific wavelengths in near-infrared spectra for which whole blood samples may be best monitored is not straightforward due to variances in the broad peaks of water and various forms of hemoglobin in such NIR spectra.

Even with the best monitoring wavelengths being chosen, one must address the variability caused by the effective path length that the transmitted or reflected near-infrared radiation takes between excitation and detection through the blood sampling. This is especially true when the blood being irradiated is constantly changing due to movement of the blood, a dynamic condition for spectral analysis. Prior efforts to employ NIR spectral analysis have either discounted the importance of determining effective path length or required procedures to establish the effective path length prior to completing the spectral analysis. In the former case, reproducible precision suffers; in the latter case, a complicated methodology is employed.

Thus, what is needed is a method for accurately determining through NIR spectral analysis in a dynamic condition a property of a sample of biological matter which is rapid, inexpensive, accurate, precise, and which takes into account such spectroscopic variabilities as effective path length of the reflected or transmitted light or where instrumentation may be using either a continuous measurement of absorbance wavelengths across a NIR spectra or at discrete wavelengths thereof.

SUMMARY OF THE INVENTION

The present invention provides a method for rapidly, inexpensively, and accurately characterizing the properties of matter of biological origin containing water by analyzing the near-infrared spectrum of the biological matter while in a dynamic condition using techniques useful with NIR spectral instrumentation and predicting the properties without sample preconditioning. The techniques seek to minimize the effect of light scattering and use mathematical regression analysis to permit transforming the observed spectrum into a prediction of the property to be analyzed.

The method of the present invention avoids chemical alteration or physical separation of the components in the sample of biological matter. The method also avoids inaccuracies caused by irrelevant variations in samples and instrumental noise in measurement techniques.

The method of the present invention is founded on the principle that the biological matter may be considered to consist of essentially two compartments: one compartment which had a proportionally different (larger or smaller) amount of water than the other compartment related to or having the property to be analyzed. The present invention is also founded on the principle that identification of the volume or weight fraction or concentration of water in the biological matter will serve as the basis for calculation of the property to be analyzed. The method of the present invention is further founded on the principle that the establishment of a training set of the combination of NIR spectra of several samples of the biological matter and the independent quantification of the property to be analyzed in each sample provides a source of mathematical comparison for accurately predicting the property to be analyzed in an unknown additional sample by using such mathematical comparison.

When the biological matter is whole blood, prediction of the hematocrit or hemoglobin concentration is achieved by obtaining near-infrared spectra of a statistically sufficient number of samples of whole blood to establish a training set for mathematical comparisons against individual additional unknown samples of other whole blood. Further, the property to be analyzed in the whole blood, e.g., hematocrit or hemoglobin concentration, is independently quantified by using an independent known technique: lysing and chemical alteration for hemoglobin and Coulter counting or centrifuging for hematocrit.

Having established a training set of NIR spectra and independently quantified the hematocrit or hemoglobin concentration in each sample in the training set, the nature of the inter-relationship between the hematocrit or hemoglobin and the water content is statistically correlated to establish the source of comparison when predicting unknown samples.

To minimize variability when establishing the training set and when predicting the properties of the compartment being analyzed in the unknown sample, a pre-processing technique is employed.

One useful pre-processing technique is disclosed in U.S. patent application Ser. No. 07/408,747, filed concurrently by one of the applicants (File UOFW-1-4265). That technique is a multiple derivative transformation of the training set spectra and the unknown sample's spectrum to minimize the effect of light scattering and other instrumental noise on the various spectra, in order to allow a mathematical correlation using the multiple derivative of the spectral intensity at a single wavelength to accurately predict the property of the compartment being analyzed in the unknown sample.

A different and useful type of pre-processing technique is disclosed in U.S. patent application Ser. No. 07/408,746, (File 44446USA8A), filed concurrently by two of the applicants. That technique is a ratio pre-processing technique which applies a ratio of an absorbance peak of the water content in the biological matter to another absorbance measuring point in order to minimize variations due to sampling techniques and instrumentation factors. This allows the accurate mathematical correlation to predict the property of the compartment being analyzed in the unknown sample.

In the case of hematocrit or hemoglobin concentration determinations, through mathematical regression analysis, it has been found that use of the absorbance peak of water appearing in NIR spectra in the range of from about 1150 to about 1190 nanometers (nm) provides an accurate and reproducible peak for multiple derivative transformation pre-processing techniques, notwithstanding a known decrease in detector efficiency using silicon detectors in this range of wavelengths. This peak of absorbance of water in the 1150–1190 nm range is largely isolated from the absorbance of hemoglobin either in its oxygenated state or in its deoxygenated state. The absorbance peak of water in this region is primarily the result of simultaneous excitation of the symmetric O-H stretch, the O-H bending mode, and the antisymmetric O-H stretch of the water molecule, whether existing in the biological matter as free water, bound to other molecules, or other forms.

While the peak of absorbance of water in the 1150–1190 nm range may be largely isolated from the absorbance of hemoglobin, it is not totally isolated. Indeed, it is preferred in the present invention to distinguish between the two principal forms of the hemoglobin component in whole blood, oxyhemoglobin and deoxyhemoglobin, and add that independent variable to the regression analysis which both establishes the training set and predicts the unknown sample's hematocrit or hemoglobin concentration.

Gathering the training set spectral data for the samples of the biological matter depends on the type of instrumentation to be employed. To establish the training set according to the present invention, the biological matter is diverted from the body of the organism and returned.

For purposes of full disclosure, a different and useful method of gathering data employing a static condition of spectral analysis is disclosed in either U.S. patent application Ser. No. 07/408,747, filed by one of the applicants (File Number UOFW-1-4265) or U.S. patent application Ser. No. 07/408,746, filed by two of the applicants (File 44446USA8A). In those instances the biological matter may be withdrawn from the body of the organism. Additionally, the biological matter may be measured within the body of the organism. However, to provide the independent quantification of the property to be analyzed from the training set samples, a sample of the biological matter must be withdrawn from the organism and often cannot be returned to the organism because of chemical alteration or physical separation of the compartment in the matter.

One embodiment of diversion and return of the biological matter to the patient is an extracorporeal loop described herein.

Gathering the unknown sample spectral data for analysis also depends on the type of instrumentation to be employed. The unknown sample may be diverted from the body of the organism for spectral detection or measurement and returned to the body, or the unknown sample may be analyzed in vivo. One embodiment of diversion and return of the biological matter to the patient is the extracorporeal loop described herein.

Processing and instrumentation variabilities are dependent upon the method by which the training set is established and the method by which the unknown samples are analyzed. In the present invention, the biological fluid is moving when being spectrally analyzed, a dynamic condition.

When the biological fluid is whole blood and the hematocrit or the concentration of hemoglobin is desired, the whole blood, either moving from the body through a optical path before returning or moving in the body, is spectrally analyzed in a dynamic condition either using diffuse transmission detection or reflectance detection as appropriate.

Because of the use of the appropriate pre-processing technique, variations due to sampling techniques of biological matter in a dynamic condition and instrumentation factors such as effective path length are minimized.

The NIR spectrum of the unknown sample is obtained from either continuous or discrete wavelength measuring instrumentation. After the spectrum is obtained and subjected to the appropriate pre-processing, the property of interest may be predicted by a mathematical correlation to the training set spectra.

In the case of the measurement of hematocrit or hemoglobin concentration in an unknown sample of whole blood, after the NIR spectrum of the unknown sample is observed and subjected to pre-processing, application of mathematical techniques comparing the training set spectral data for the hematocrit or the hemoglobin concentration with the unknown sample's spectra allows prediction of the hematocrit or the hemoglobin concentration in the unknown sample.

For an additional appreciation of the scope of the present invention, a more detailed description of the invention follows, with reference to the drawings.

EMBODIMENTS OF THE INVENTION

One embodiment of the present invention is the analysis of hematocrit in whole blood. Another embodiment of the present invention is the analysis of hemoglobin concentration in whole blood. There are occasions when either analysis may be preferred. But generally, it is recognized that the determination of hematocrit is an excellent correlation to the concentration of hemoglobin in whole blood. However for versatility of the system, it should be recognized that one or more methods of independent quantification of the property to be analyzed may be used to provide alternative clinical diagnosis of the condition of the patient.

It should also be recognized that the property of the biological matter to be analyzed must have some correlation either positively or negatively with the water content in order to develop a mathematical correlation therefor in accordance with the present invention. That may not preclude the presence of other components in de minimus volume fractions or concentrations. For example, in whole blood, the presence of white blood cells, platelets, hydrocarbonaceous lipids, and the like are not present in sufficient quantity at the desired level of precision to destroy the validity of the mathematical correlation found. However, as described below, the determination of the oxygen saturation in the whole blood may distinguish between oxyhemoglobin and deoxyhemoglobin, in order to predict the property of interest with greater accuracy.

SPECTROSCOPIC INSTRUMENTATION

Figure 1:
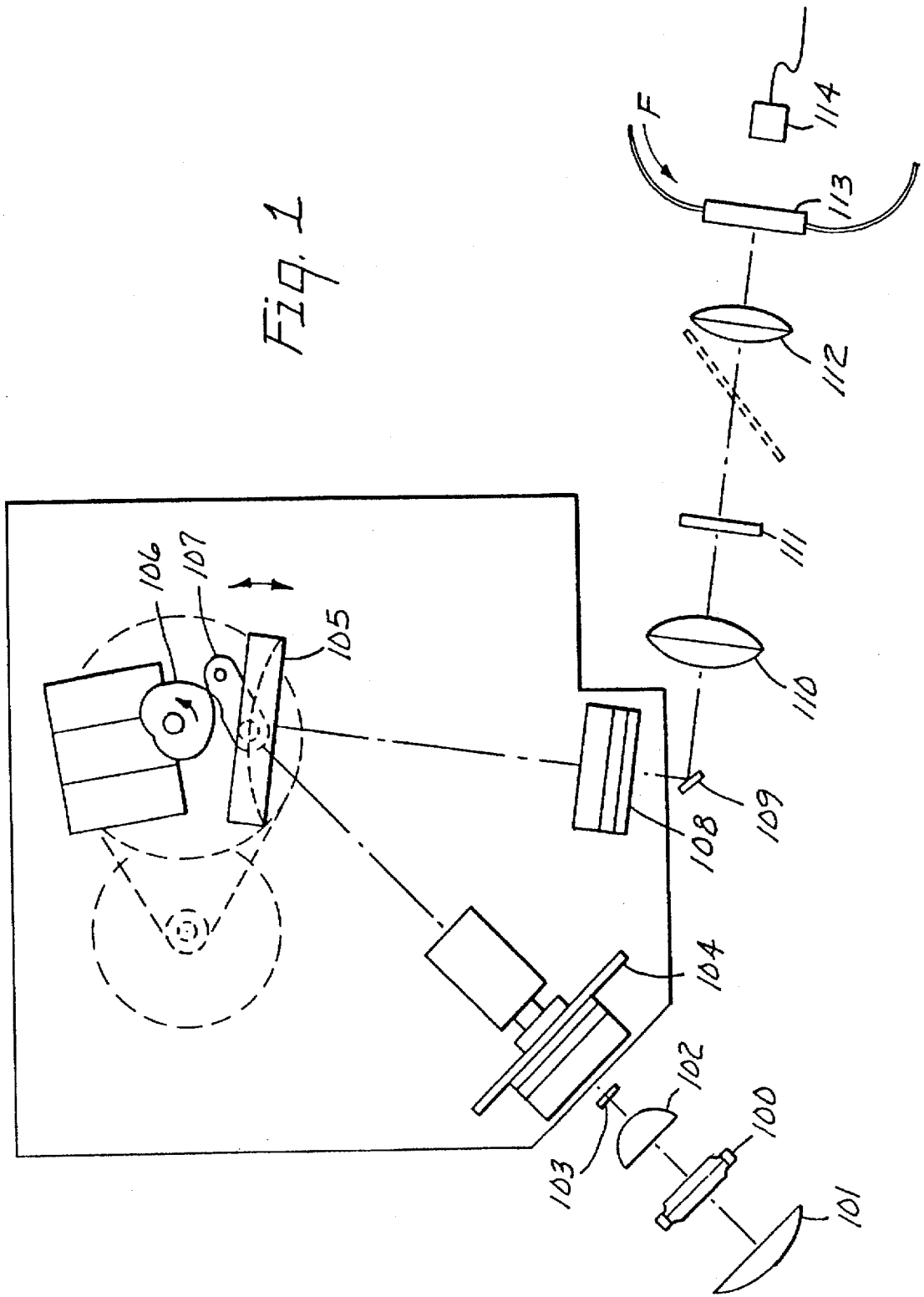
FIG. 1 is a schematic block diagram of the instrumentation useful in a method carried out in accordance with the present invention.

FIG. 1 identifies the schematic block diagram of spectral instrumentation useful in establishing the training set initially and thereafter predicting the property of the compartment to be analyzed in one or more unknown additional samples.

FIG. 1 illustrates a typical instrumentation system available which can be used for obtaining the near infrared spectrum of a biological fluid, such as whole blood. Specifically, FIG. 1 identifies a Model 6250 spectrophotometer manufactured by Near Infrared Systems of Silver Spring, Md., formerly known as Model 6250 made by Pacific Scientific. The radiation from a tungsten lamp 100 is concentrated by a reflector 101 and lens 102 on the entrance slit 103 and thereafter passed through an order sorting filter 104 before illuminating a concave holographic grating 105 to disperse the radiation from the tungsten lamp 100 onto the sample 113 in a dynamic condition in an optical blood loop or in the body of the organism. The grating 105 is where the wavelength dispersion occurs. The grating is scanned through the desired wavelength range, typically 680 to 1235 nanometers, by the rotating cam bearing 106, which is coupled to the grating by linkage assembly 107. The selected wavelength passes through exit slit 108 and is guided through the cell 113 through which the sample is moving in direction F, by mirror 109, iris 111, and lenses 110 and 112. After passing through the sample, the remaining radiation is converted to an electrical signal by detector 114.

Other types of instrumentation are also acceptable for use with the methods of the present invention. Monochromators such as Model HR 320 available from Instruments S.A. are useful. Polychromators such as the Chemspec Model 100S available from American Holograph or Model JY320 also available from Instruments S.A. may be used to gather the spectral data to establish the training set.

Detection means may employ either diffuse transmittance detection devices or reflectance devices available commercially. The Model 6250 spectrophotometer may be configured to detect either diffuse transmittance or diffuse reflectance. Depending on factors such as cost, wavelength range desired, and the like, the detector 114 may be a silicon detector, a gallium arsenide detector, a lead sulfide detector, an indium gallium arsenide detector, a selenium detector or a germanium detector.

Whichever detector is chosen, it is preferred to be consistent in the usage of same detection means for establishing the training set spectra and for measuring the unknown sample's spectrum.

Alternately, polychromatic analyzers using a reversed beam geometry may be used to disperse the transmitted or reflected light into its spectral components and photodiode arrays may be used to detect or measure the dispersed light at different positions along the output spectral plane.

Other types of array detectors include charge coupled devices, charge injection devices, silicon target vidicons, and the like. Desirably, the polychromatic analyzer should include an entrance slit that defines the bandwidth of light which is consistent with the spectal resolution desired. One commercially available photodiode array useful with the present invention is Model 1024S photodiode array available from Reticon, Inc., which consists of 1024 diodes of 25 micron width and 2.5 millimeters height. That photodiode array may be used in a complete spectral detection system such as Model ST120 available from Princeton Instruments.

One can also use interference filters as spectroanalyzers, for example, by passing a series of discrete wavelength interference filters one at a time before a suitable detector. It is also possible to use interferometers or a Hadamard transform spectrometer to analyze the diffuse light.

The above detection means are based on detection of spectra from a broad band light source. However, if narrow band sources of NIR light are to be used, such as tungsten lamps with interference filters, light emitting diodes, or laser (either a single tunable laser or multiple lasers at fixed frequencies), other detection techniques may be used. For example, the input signal can be multiplexed either in time, (to sequence each wavelength), or in wavelength (using sequences of multiple wavelengths), and thereafter modulated and the collected signals demodulated and demultiplexed to provide individual wavelength signals without the need for optical filtering.

Regardless of the spectroscopic instrumentation selected, it is preferred to use a computer connected to the instrument to receive the spectral data, perform the analysis described below, and provide a printout or readout of the value of the property predicted. When using spectrometric instruments such as the Model 6250 spectrometer described above, a personal computer such as a "PS/2" Model 50 computer from IBM of Boca Raton, Fla. is used and preferred.

MULTIPLE DERIVATIVE PRE-PROCESSING TECHNIQUE AFTER DYNAMIC CONDITION SPECTRAL DATA GATHERING

Figure 2:
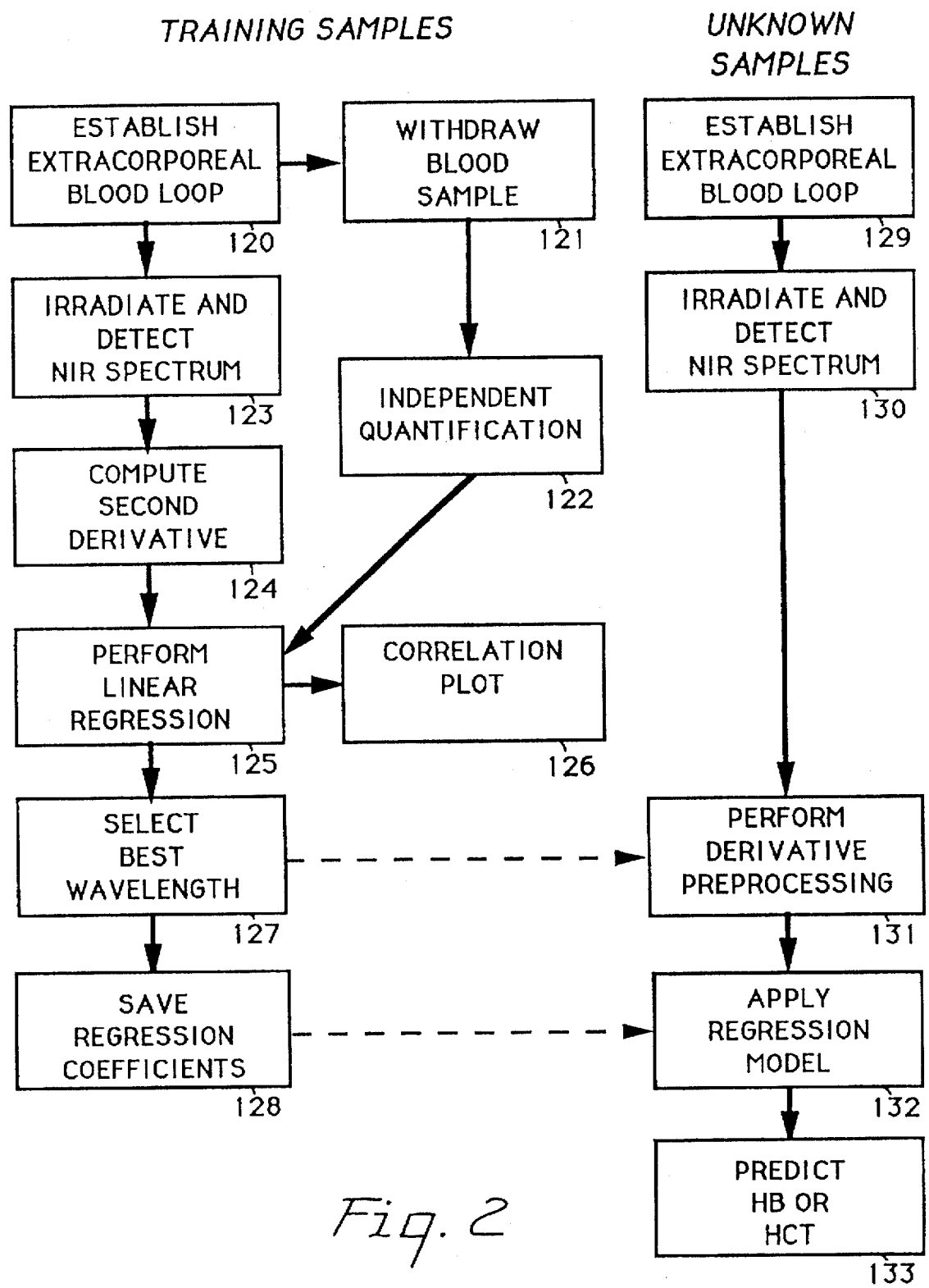
FIG. 2 is a schematic flow chart of the methods to mathematically minimize variability of spectral data using multiple derivative transformation techniques and establish the mathematical correlation between known samples and the training set spectra, in order to permit the predicting of the property of interest in an unknown sample by comparison with the mathematical correlation.

FIG. 2 is a schematic flow chart of the method of the present invention using for pre-processing the multiple derivative transformation pre-processing technique disclosed in U.S. patent application Ser. No. 07/408,747, (File UOFW-1-4265), which pre-processing is employed to minimize sample and instrumentation variability. The regression analysis of the method identifies the nature of the mathematical correlation between the property to be analyzed in the first compartment and the water content in the biological matter, in order to predict the property of the compartment to be analyzed in an unknown sample.

The schematic flow of the processing steps involved in determining the property of interest in the biological matter, such as hematocrit or hemoglobin concentration, can be broadly divided into two parts: steps 120 to 128 which comprise the training phase of the analysis and steps 129 to 133 which comprise the prediction of the property of an unknown sample.

The training or calibration development phase consists of observing a series of blood samples 120 by diverting the samples from one or more animals of the same species through a blood loop or by otherwise observing the samples in the organisms. Additionally, for the independent quantification of property of interest, samples are obtained by withdrawing blood, step 121, from each of the animals participating in step 120.

The samples of steps 120 and 121 are analyzed on two parallel paths.

The first path consists of independent quantification of the property of interest, step 122. It is important that the independent quantification be done accurately. The accuracy of the method of the present invention is dependent upon the accuracy of the independent quantification step 122 because validation of the mathematical correlation is based on the independently quantified value of the property of interest.

The second path consists of irradiating the samples with infrared light and detecting the near infrared spectrum for each sample, step 123, and then computing the second derivative of the spectra, step 124. It should be understood that reference to detecting the near infrared spectrum involves both the measurement of diffusely transmitted or reflected spectrum and the transformation of that spectrum to an absorbance spectrum. The transformation is based on having taken a spectrum of the cell containing only air for calibration purposes.

When the near infrared spectrum has been detected on a Near Infrared Systems Model 6250 spectrophotometer, the near infrared spectrum from 680 to 1235 nanometers consists of 700 individual absorbance measurements. The second derivative transformation preprocessing step computes less than the total 700 measurements because some transformations are not available at the edges of the spectra. When using software such as "Near Infrared Spectral Analysis" commercially available from Pacific Scientific, now known as Near Infrared Systems of Silver Spring, Md., one may compute an approximated derivative by using finite difference approximations. Different approximations may yield different derivative spectra and different transformation equations. In such software, different approximations may be adjusted according to segment of the spectrum being measured and the gap between segments being measured. Using different derivative approximations may result in a different set of regression coefficients that may affect the accuracy or precision of the prediction of the property being analyzed. It is therefore prudent to evaluate a wide range of segments and gaps in order to ascertain which selection is best for the particular analysis contemplated.

The preprocessed spectra for the set of training samples subjected to second derivative transformation, step 124, are correlated with the values obtained during the independent quantification step 122 by using a mathematical regression technique, step 125, such as linear regression. The second derivative value providing the best correlation of calculated value to actual value is generally the wavelength chosen for the mathematical correlation.

One of the outputs of this regression step is a correlation plot, step 126, which graphically shows the wavelengths of the spectrum where the highest correlation is found. The best transformed wavelength in the water band region of 1150 to 1190 nm, step 127, is selected by identifying the peak of optimum correlation. The regression coefficients corresponding to the selected wavelength are saved, step 128, for future application to the analysis of individual samples to predict the property of interest.

The steps 129 to 133 in FIG. 2 show the procedure to be followed for predicting hematocrit (abbreviated as HCT in FIG. 2) or hemoglobin (abbreviated as HB in FIG. 2) concentration in an individual unknown sample. A blood sample of unknown hematocrit or hemoglobin concentration, step 129, is observed by viewing the blood in an extracorporeal blood loop or in the organism, and the near infrared spectrum of this sample is detected or measured, step 130.

While the near infrared spectrum of additional unknown samples may also be detected on exactly the same instrument as the training samples were detected and from which the training set is prepared, it is also acceptable to use a simpler instrument which will provide the absorbance at only the three minimal wavelengths necessary to compute a second derivative transformation of the best wavelength.

The second derivative intensity for the best wavelength determined in step 127 is computed for the unknown sample, step 131. Then the regression coefficients contained in the mathematical correlation, determined during the training procedure and saved in step 128, are applied to the second derivative wavelength obtained for the additional individual unknown blood sample 132, in order to yield the predicted hematocrit or hemoglobin concentration, step 133.

The pre-processing technique of multiple derivative transformation serves to eliminate the variances of spectral data caused by scatter in each of the various samples of both the training set and each unknown sample. This scatter would otherwise disrupt the accuracy of the detection of the training set spectra and its ability to predict the property of the unknown sample.

If the near infrared spectrum consists of N individual wavelengths, computing the second derivative transformation provides N spectral features less the loss of the features at the edges of the spectrum. In FIG. 2, such computation is shown at step 124. The best wavelength must be chosen from the myriad of N transformed wavelengths using regression mathematical techniques, as is shown in FIG. 2 at step 125, depicted in a correlation plot at step 126, and selected at step 127 for use to determine the best possible regression coefficients in step 129 and for use with each unknown sample in step 132.

Any of a number of regression techniques; such as, linear regression, multiple linear regression, stepwise regression, partial least squares regression, or principal component regression can be used to develop a statistical correlation between the ratio spectral features and the variable of the property being quantified. Such regression techniques are available by reference to such literature as Draper and Smith, *Applied Regression Analysis,* Wiley and Sons, New York, 1982 and Geladi and Kowalski, *Analytica Chimica Acta,* Volume 185, pp 1–17 and 19–32, 1986, the disclosures of which are incorporated by reference.

In order to determine the best wavelength for a given application, regression models are computed against all of the possible N transformed wavelengths.

Each regression model is evaluated by using an accepted statistical measure. For example, one useful measure is the simple correlation coefficient computed from the actual hematocrit value obtained from the independent quantification and the predicted hematocrit value obtained from the regression model, as is shown in FIG. 2 at step 127.

A correlation plot can be constructed to visually show which wavelength involving the absorbance of water provides the highest correlation, as is shown in FIG. 2 at step 127. A representative correlation plot for hemoglobin appears as FIG. 6. It is important to consider both high correlation and also the sensitivity of the correlation obtained to measure small changes in the actual wavelengths.

RATIO PRE-PROCESSING TECHNIQUE AFTER DYNAMIC CONDITION SPECTRAL DATA GATHERING

Figure 3:
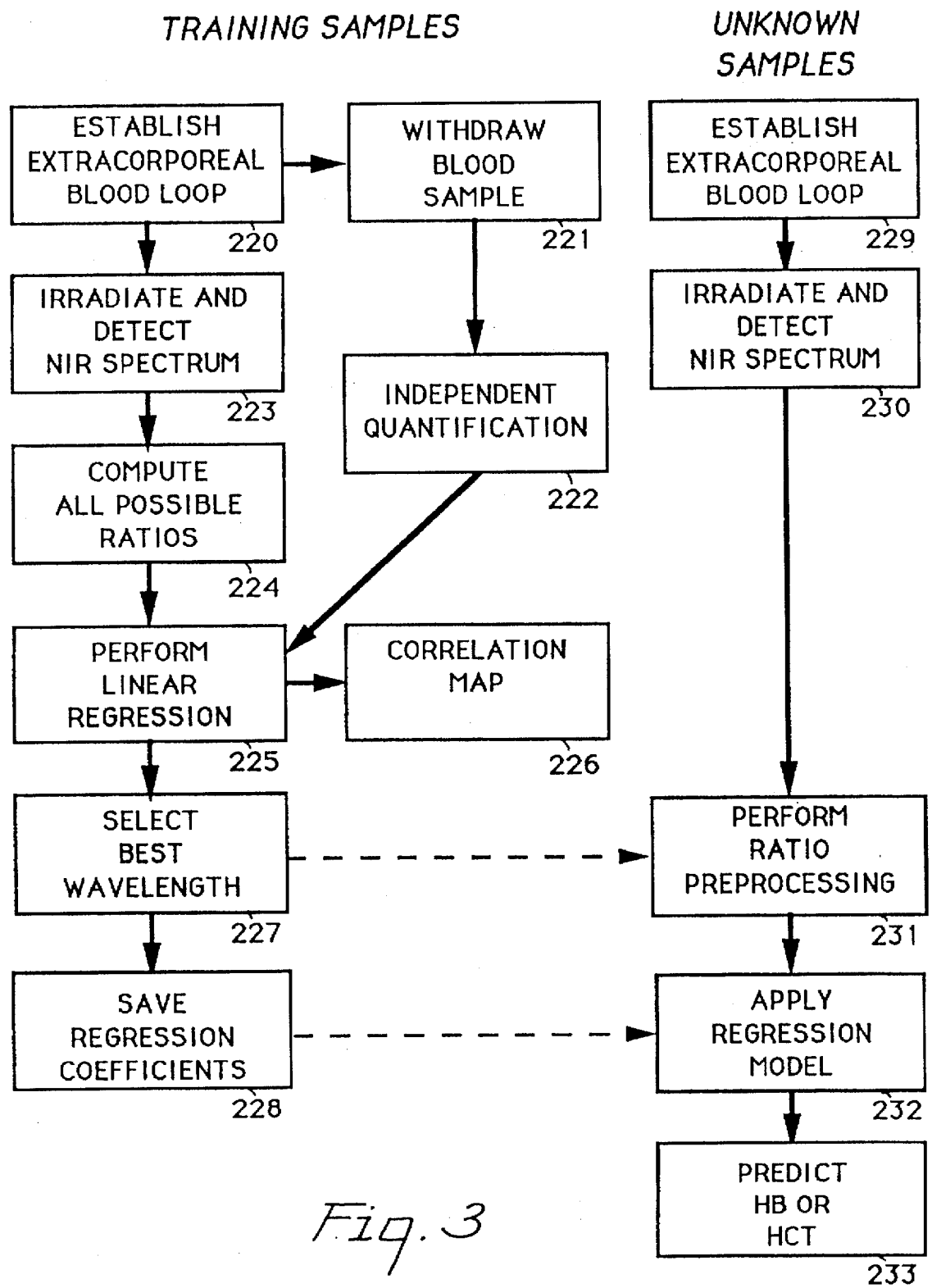
FIG. 3 is a schematic flow chart of the methods to mathematically minimize variability of spectral data using ratioing techniques and establish the mathematical correlation between known samples and the training set spectra, in order to permit the predicting of the property of interest in an unknown sample by comparison with the mathematical correlation.

FIG. 3 is a schematic flow chart of the method of the present invention using for pre-processing the ratio pre-processing technique described herein and also disclosed in U.S. patent application Ser. No. 07/408,746, (File 44446USA8A), which pre-processing is employed to minimize sample and instrumentation variability. The regression analysis of the method identifies the nature of the mathematical correlation between the property to be analyzed in the first compartment and the water content in the biological matter, in order to predict the property to be analyzed in an unknown sample.

The schematic flow of the processing steps involved in determining the property of interest in the biological matter, such as hematocrit or hemoglobin concentration, can also be broadly divided into two parts: steps 220 to 228 which comprise the training phase of the analysis and steps 229 to 233 which comprise the prediction of the property of an unknown sample.

The training or calibration development phase consists of observing a series of blood samples 220 by diverting the samples of one or more animals of the same species through a blood loop or by otherwise observing the samples in the organisms. Additionally, for the independent quantification of property of interest, samples are obtained by withdrawing blood, step 221, from each of the animals participating in step 220.

The samples of steps 220 and 221 are analyzed on two parallel paths.

The first path consists of independent quantification of the property of interest, step 222. It is important that the independent quantification be done accurately. The accuracy of the method of the present invention is dependent upon the accuracy of the independent quantification step 222 because validation of the mathematical correlation is based on the independently quantified value of the property of interest.

The second path consists of irradiating the samples with infrared light and detecting the near infrared spectrum for each sample, step 223, and then computing all possible ratios of two wavelengths in the spectrum, step 224.

When the near infrared spectrum has been detected on a Near Infrared Systems model 6250 spectrophotometer, the near infrared spectrum from 680 to 1235 nanometers consists of 700 individual absorbance measurements. The pre-processing step of computing all possible ratios of two wavelengths expands the 700 point spectrum into 700*700 or 490,000 ratio pairs. Since near infrared spectra consist of broad, slowly changing absorbance bands, computing the ratio terms using every fifth data point, 140 point spectrum, results in equivalent performance with a significant decrease in the overall computation requirement, 140*140 or 19,600 ratio terms.

The preprocessed spectra for the set of training samples consisting of the calculated ratios, step 224, are correlated with the values obtained during the independent quantification step 222 by using a mathematical regression technique, step 225, such as linear regression. The pair providing the best correlation of calculated values to actual values is generally the pair of wavelengths chosen for the ratio in the mathematical correlation.

One of the outputs of this regression step is a correlation map, step 226, which graphically shows the regions of the spectrum where the most useful ratio pairs are found. The best ratio pair, step 227, is selected by identifying a region of high correlation which is also independent of small changes in the actual wavelength selected. The regression coefficients corresponding to the selected ratio pair are saved, step 228, for future application to the analysis of individual samples of unknown analyte content.

The steps 229 to 233 in FIG. 3 show the procedure to be followed for predicting hematocrit (abbreviated as HCT in FIG. 3) or hemoglobin (abbreviated as HB in FIG. 3) concentration in an individual unknown sample. A blood sample of unknown hematocrit or hemoglobin concentration, step 229, is observed in a dynamic condition and the near infrared spectrum of this sample is detected or measured, step 230.

While the near infrared spectrum of additional unknown samples may also be detected on exactly the same instrument as the training samples were measured and from which the training set spectra is prepared, it is also acceptable to use a simpler instrument which will provide the absorbance at only the two wavelengths selected to form the best ratio pair.

The ratio of the absorbance readings for the selected pair of wavelengths determined in step 227 is computed for the unknown sample, step 231. Then the regression coefficients contained in the mathematical correlation, determined during the training procedure and saved in step 228, are applied to the ratio obtained for the additional individual unknown blood sample 232, in order to yield the predicted hematocrit or hemoglobin concentration, step 233.

The ratio pre-processing technique serves to eliminate the variances of spectral data caused by scatter or other multiplicative errors in each of the various samples of both the training set and each unknown sample. This scatter would otherwise disrupt the accuracy of the detection of the training set spectra and its ability to predict the property in the unknown sample. Because both wavelengths in the selected best pair of wavelengths used in the ratio experience the same path length, variations in the effective path length due to scatter are minimized.

If the near infrared spectrum consists of N individual wavelengths, computing all possible ratios of each pair of wavelengths provides N*N new spectral features. In FIG. 3, such computation of all possible ratios is shown at step 224. The best possible ratio pair of wavelengths must be distilled from the myriad of combinations using regression mathematical techniques, as is shown in FIG. 3 at step 225, depicted in a correlation map at step 226, and selected at step 227 for use to determine the best possible regression coefficients in step 228 and for use with each unknown sample in step 231.

Any of a number of regression techniques; such as, linear regression, multiple linear regression, stepwise regression, partial least squares regression, or principal component regression can be used to develop a statistical correlation between the ratio spectral features and the variable of the analyte being quantified. Such regression techniques are available by reference to such literature as Draper and Smith and Geladi and Kowalski publications described and incorporated above for use in multiple derivative transformation. In order to determine the best ratio for a given application, regression models are computed against all possible ratio pairs of wavelengths.

Each regression model is evaluated by using an accepted statistical measure. For example, one useful measure is the simple correlation coefficient computed from the actual hematocrit value obtained from the independent quantification and the predicted hematocrit value obtained from the regression model, as is shown in FIG. 3 at step 228.

A correlation map can be constructed to visually show which wavelength ratios provide the highest correlation, as is shown in FIG. 3, at step 226. A representative correlation map for hemoglobin appears as FIG. 7. It is important to consider both high correlation and also the sensitivity of the correlation obtained to measure small changes in the actual wavelengths. The best overall ratio is found by selecting the pair of wavelengths which provide high correlation and which occur in a reasonably flat region of the correlation map.

ANALYSIS AND VALIDATION

Use of the spectral analytical instrumentation described above and depicted in FIG. 1 and either of the mathematical methods described above and depicted in FIGS. 2 and 3 permit the analysis of the property of interest in the biological matter which contains water, so long as it is possible to develop a mathematical correlation between that property and water when establishing the training set through independent quantification of the property, spectra of the samples and use of the appropriate pre-processing techniques to minimize variability.

The determination of the mathematical correlation or model is founded on the linear functional relationship of the multiple linear regression equation:

$$B_0 + B_1(A_1) + B_2(A_2) + \ldots B_n(A_n) = C$$

where $B_0$ is the intercept, $B_n$ is the regression coefficient for the nth independent variable, $A_n$ is the nth independent variable and C is the value of the property of interest to be analyzed. Solving this equation depends upon the determination of regression coefficient(s) including the intercept and providing the values of the independent variable(s).

When the linear functional relationship is less complex, the equation is more often expressed as the linear regression equation: $Y = mx + b$, where Y is the value of the property of interest to be analyzed, m is the regression coefficient indicating the slope of the line, b is the intercept of the line and x is the single independent variable. Thus, the mathematical correlation endeavors to yield a linear relationship between the single independent variable, which is the multiple derivative transformed intensity or the ratio of the two best absorbance pairs, and the property of interest to be measured.

The linear functional relationship is more complex and involves more than one independent variable when the effect of oxygen saturation is used to adjust the mathematical correlation of hematocrit or hemoglobin concentration to the water content in whole blood. Then, the equation is expressed as a multiple linear regression equation:

$$C = B_0 + B_1(A_1) + B_2(A_2),$$

where C is the hematocrit or hemoglobin concentration; $B_0$ is the intercept; $B_1$ is the regression coefficient for the percent oxygen saturation; $A_1$ is the percent oxygen saturation; $B_2$ is the regression coefficient of the independent variable determined from either the multiple derivative transformation or the ratioing preprocessing.

Once the mathematical correlation is established, it is validated. The accuracy in formation and performance is reviewed to assure reproducibility. The accuracy and precision of the mathematical correlation can be validated by physical interpretation of the selected spectral features or using additional samples analyzed by independent quantification, step 122 of FIG. 2 or step 222 of FIG. 3, and then subjecting those samples to steps 129–133 of FIG. 2 or steps 229–233 of FIG. 3, as if the samples were unknown. Statistical methods may then be used to compare the value of the predicted property, step 133 or step 233, and the value determined by independent quantification, step 122 or step 222, to confirm reproducibility.

Standard error of calibration measures precision of formation of the model of the training set spectra, i.e., how well the regression analysis performs with the data used to construct the training set. The standard error of calibration (SEC) can be calculated from the following equation:

$$SEC = \left[ \frac{1}{N_T - n - 1} \sum_{i=1}^{N_T} (C_i - c_i)^2 \right]^{1/2}$$

where N is the number of training samples, n is the number of absorbance terms in the regression technique employed, where $c_i$ is the hematocrit value of the ith sample as calculated during linear regression and $C_i$ is the hematocrit value of the ith sample as independently determined. The smaller the SEC, the more precise the model mathematical correlation has been formed.

More importantly, the standard error of prediction (SEP) measures the assurance of reproducible performance, i.e., a test to identify quantitatively the accuracy and precision of the prediction results obtained using the method of the present invention with the actual value for the property determined by independent quantification using known and accepted techniques and may be used in conjunction with a confidence limit to quantitatively express the accuracy of the prediction of the property being analyzed. Mathematically, the standard error of prediction can be calculated from the following equation:

$$SEP = \left[ \frac{1}{N_P - n - 1} \sum_{i=1}^{N_P} (C_i - c_i)^2 \right]^{1/2}$$

where N is the number of validation samples, $C_i$ is the independently quantified value for the ith validation sample $c_i$ is the value for the ith validation sample obtained using the mathematical correlation of step 131. Also, the smaller the SEP, the more accurate and precise the prediction.

Bias measures the extent of deviation of all points within a given data set in the solved mathematical equation from the line of exact correlation between predicted and actual values. Qualitatively, a low bias indicates the presence of a robustness of the training set spectra to tolerate possible error. In other words, the robustness of the training set sampling anticipates the variety of sampling possibilities for the unknown sample and minimizes its effect.

INDEPENDENT VARIABLE BASED ON OXYGEN SATURATION OF HEMOGLOBIN

As stated above with reference to the flow charts depicted in FIGS. 2 and 3, the regression analysis may employ multiple variables according to the equations described above.

One multiple variable of assistance to the prediction of the property of interest is the percentage oxygen in the hemoglobin of whole blood, which distinguishes the hemoglobin between its oxy and deoxy forms. Because oxy and deoxy hemoglobin have different spectra, including in the region of 1150–1190 nm, the assessment of the relative contributions of both forms of hemoglobin, or a value proportional to their relative contributions, allows the adjustment of the mathematical correlation being developed for the prediction of hematocrit or hemoglobin concentration.

Figure 10:
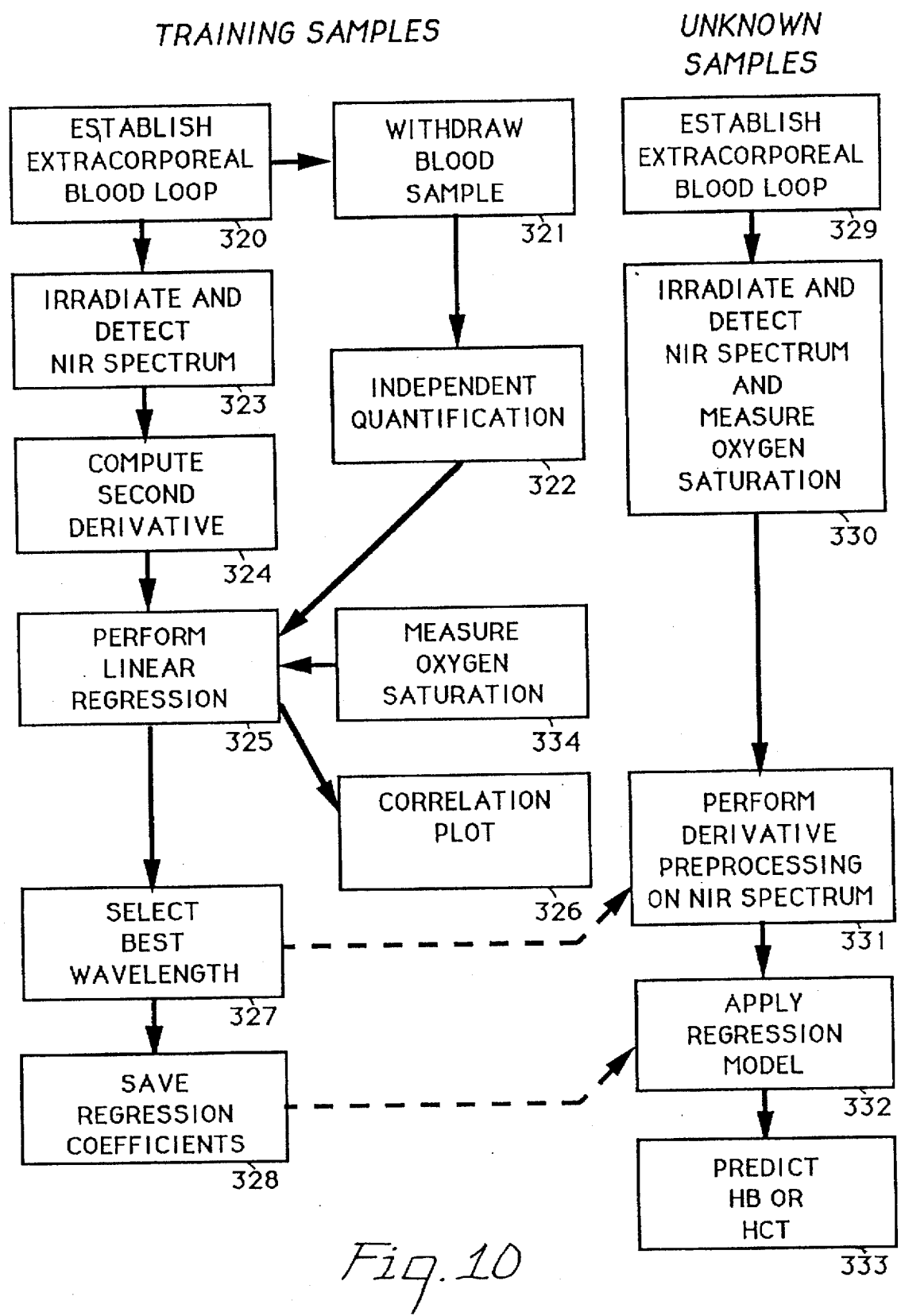
FIG. 10 is a schematic flow chart, similar to FIG. 2, of another method of the present invention to mathematically minimize variability of spectral data using multiple derivative transformation techniques and adjustment for the different forms of hemoglobin.
Figure 11:
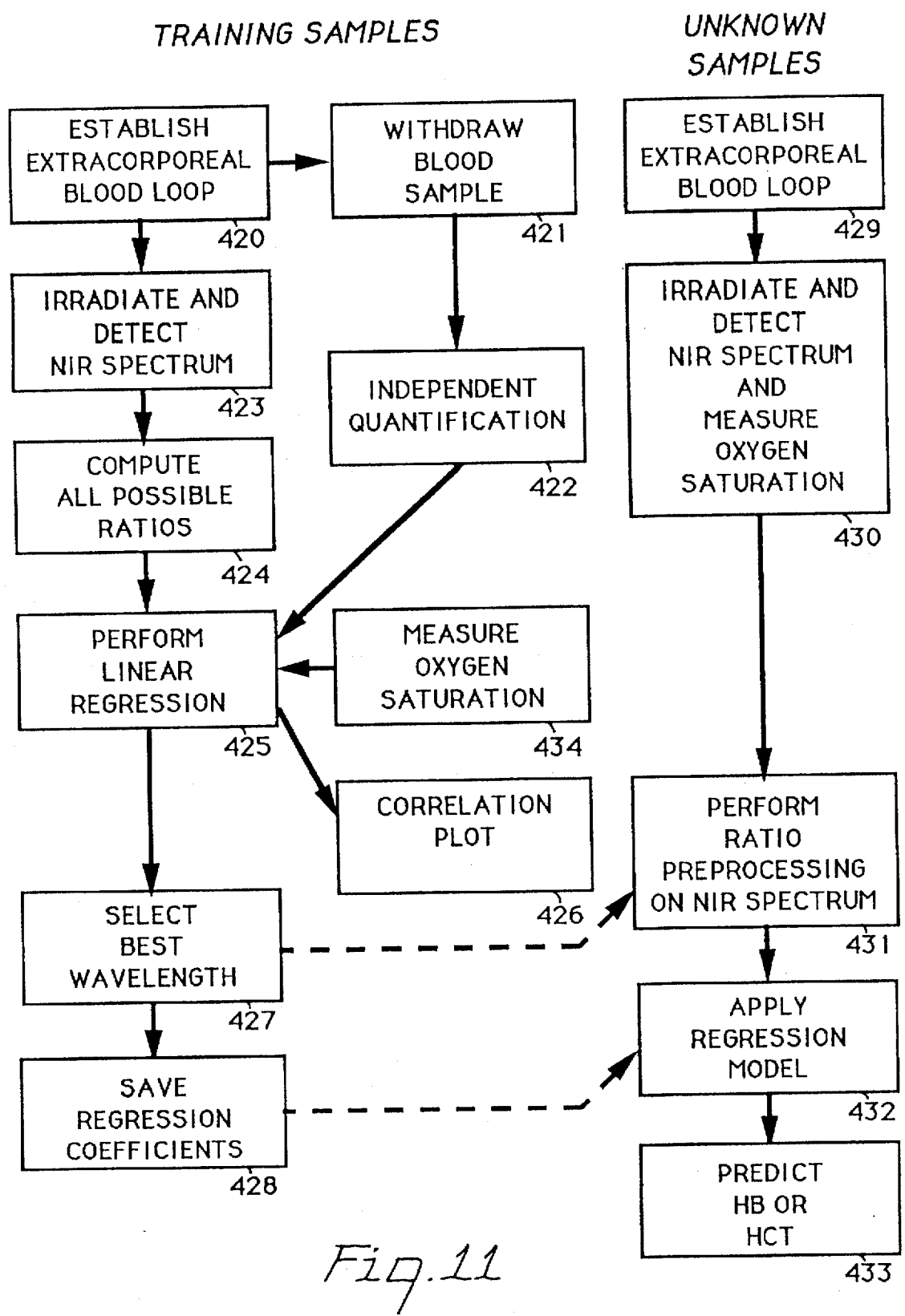
FIG. 11 is a schematic flow chart, similar to FIG. 2, of another method of the present invention to mathematically minimize variability of spectral data using ratioing techniques and adjustment for the different forms of hemoglobin in the whole blood.

FIGS. 10 and 11 depict the schematic flow charts, similar to FIGS. 2 and 3, respectively. Reference numbers 320–333 in FIG. 10 depicts the same steps as reference numbers 120–133 in FIG. 2. Reference numbers 420–433 in FIG. 11 depicts the same steps as reference numbers 220–233 in FIG. 3. FIGS. 10 and 11 add the steps in the method to adjust the mathematical correlation and the prediction to account for percent oxygen saturation in the whole blood. As may be seen in FIG. 10, measurement of oxygen saturation or a value proportional to oxygen saturation, step 334, is added to assist in performing the linear regression, step 325, and step 330 is modified to include the measurement of the oxygen saturation or a value proportional to oxygen saturation in the unknown sample. Likewise, measurement of oxygen saturation or a value proportional to oxygen saturation, step 434, is added to assist in performing the linear regression, step 425, and step 430 is modified to include the measurement of the oxygen saturation or a value proportional to oxygen saturation in the unknown sample. These alterations provide the adjustment of the independent variable, percent oxygen saturation or a value proportional to oxygen saturation, to the other independent variable, the multiple derivative transformed spectral intensity at the best wavelength or the best ratio.

The effect of percent oxygen saturation or a value proportional to oxygen saturation as an independent variable is linear throughout the percent oxygen saturation range. However, as percent oxygen saturation approaches 100 percent, the magnitude of the adjustment provided by this independent variable is progressively smaller, such that it becomes within the level of accuracy of the independent quantification itself.

Thus, for fully oxygenated patients, the use of the percent oxygen saturation independent variable in the mathematical correlation is optional. For less than fully oxygenated patients, the use of the percent oxygen saturation independent variable in the mathematical correlation is preferred. In emergency conditions, whether it is known if the patient is fully oxygenated is problematic. Therefore, for analysis of hematocrit or hemoglobin concentration, it is generally preferred to include percent oxygen saturation as an independent variable in the mathematical correlation.

Instruments to measure oxygen saturation of the hemoglobin concentration at the same time as the spectrum of whole blood is analyzed includes such commercially available instrumentation as a co-oximeter, a pulse oximeter, or other device which measures the oxygen saturation known to those skilled in the art. Co-oximetry typically involves measurement of oxygen saturation in a static condition. However, the art has progressed to measuring oxygen saturation in flowing blood such as that shown in U.S. Pat. No. 4,745,279.

Another method of measuring the second independent variable as a value proportional to percent oxygen saturation for purposes of the regression analysis depicted in FIG. 10 at 334 and 330, respectively and FIG. 11 at 434 and 430, respectively, is to employ a ratio of absorbances at two wavelengths. In other words, the value proportional to percent oxygen saturation is the ratio of the absorbances of two wavelengths where the ratio of the extinction coefficients for oxyhemoglobin and deoxyhemoglobin at one wavelength is different than that ratio at the second wavelength. Desirably, the ratio uses the absorbance of a wavelength where the extinction coefficients of oxy and deoxy hemoglobin are different, (for example at from about 680 nm to 720 nm), to the absorbance of a wavelength where the extinction coefficients of oxy and deoxy hemoglobins are the same, the isosbestic point. Use of the ratio of this spectral data obviates the need for additional oxygen saturation instrumentation.

Figure 8:
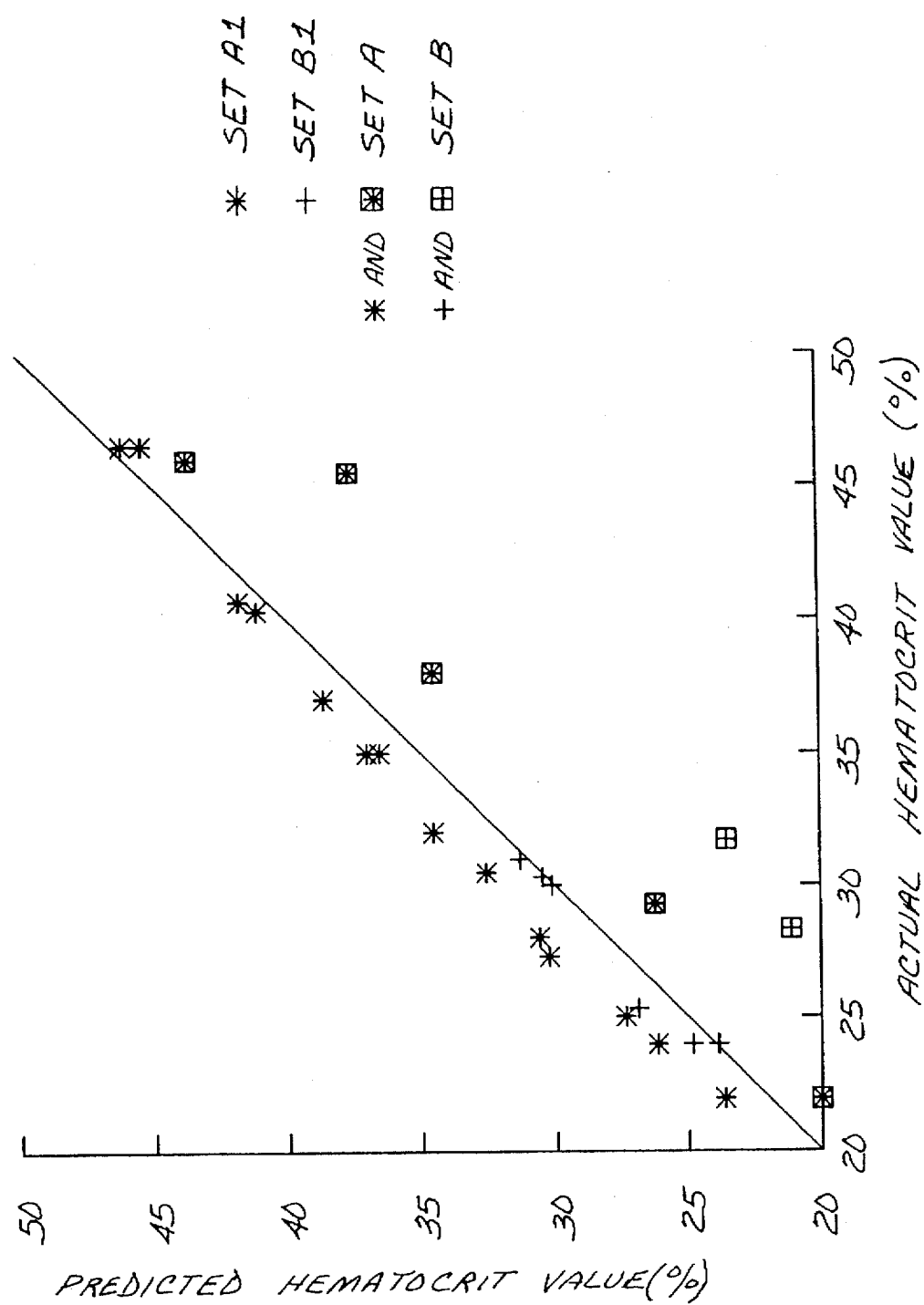
FIG. 8 is a graph showing the accuracy of prediction of hematocrit after multiple derivative transformation pre-processing compared with actual hematocrit values determined by prior art methods.
Figure 12:
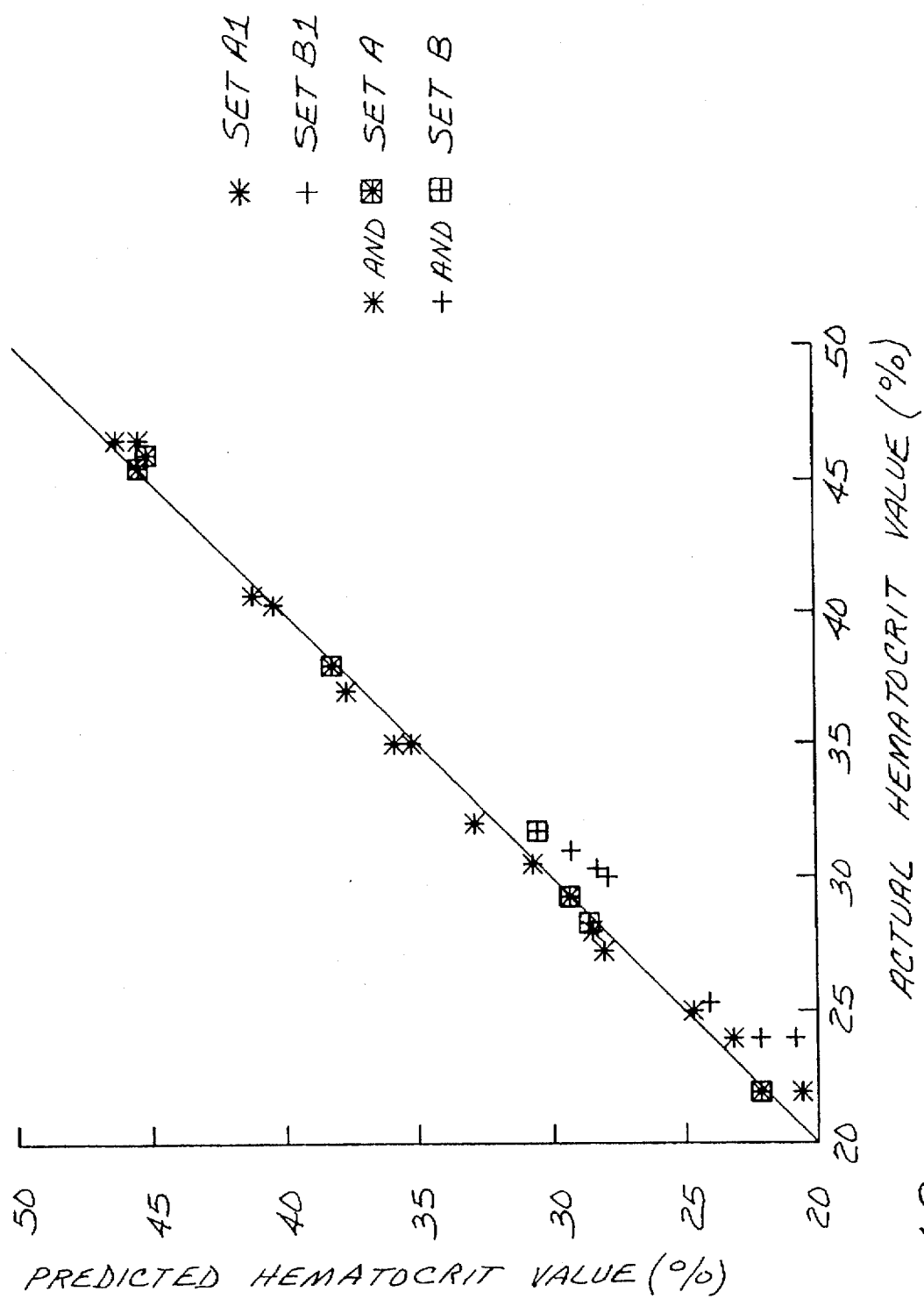
FIG. 12 is a graph showing the accuracy of prediction of hematocrit after multiple derivative transformation pre-processing and adjusting for the different forms of hemoglobin present in the whole blood, compared with actual hematocrit values determined by prior art methods.

The comparison of predicted vs. actual hematocrit or hemoglobin concentration may be graphed when the percent oxygen saturation is included as an independent variable. FIG. 12 shows a graph of predicted hematocrit against actual hematocrit. A comparison of FIG. 8 and FIG. 12 shows how the multiple independent variable mathematical correlation is generally more accurate.

Inclusion of the second variable in the regression equation serves to minimize even further any effects of oxygen saturation in the hemoglobin on the absorbance of the spectra at 1150–1190 nm. Thus, the development of a mathematical correlation which includes oxygen saturation as an independent variable enhances rather than substitutes for the method of the present invention to determine a property of interest based on its relationship to the water content in the whole blood.

EXTRACORPOREAL BLOOD LOOP A DYNAMIC CONDITION

An embodiment of the analysis of a property of interest in a biological fluid in a dynamic condition employs an extracorporeal blood loop. This blood loop permits "real time" monitoring of the changes in the values of the property of interest in whole blood.

Figure 14:
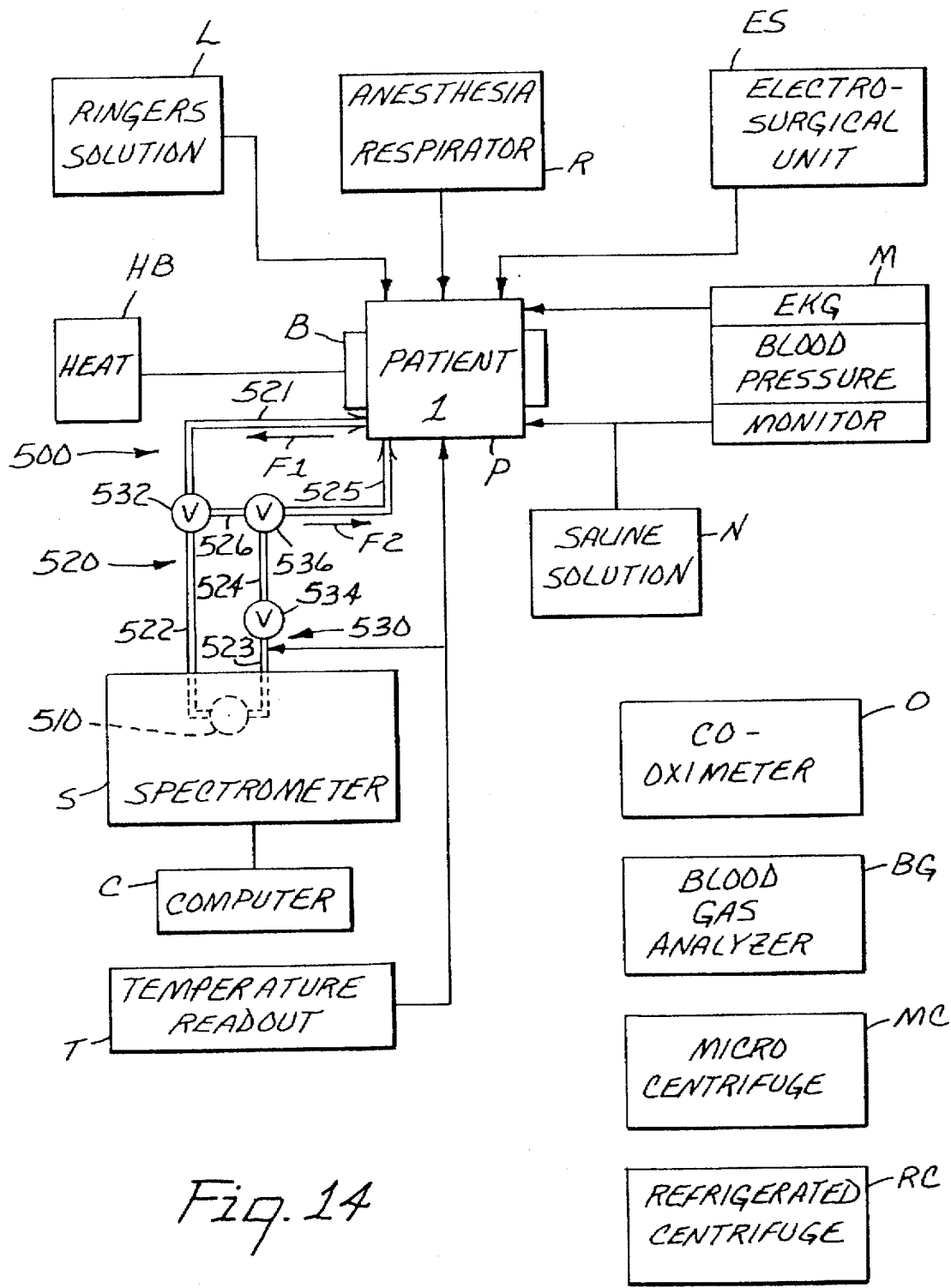
FIG. 14 is a schematic depiction of the components of the extracorporeal blood loop of the present invention.

When treating a patient during an operation such as open-heart surgery, a blood loop is used for oxygenation of the blood and to maintain adequate circulation. Adaptation of the equipment such as that described in FIG. 1 permits the analysis of hematocrit and hemoglobin concentration according to the methods of the present invention while the blood is moving from the body of the patient and being returned to the body of the patient. FIG. 14 identifies schematically the type of blood loop of the present invention using reference numerals while the other equipment necessary for the experiments described in the examples are identified by reference letters.

Referring to FIG. 14, the loop 500 is formed by connecting flow through cell 510 in the spectrometer S, also seen in FIG. 1 as item 113, tubing, generally 520, and valves, generally 530. The loop 500 may be separately configured to the patient P or may form a subloop to the loop already established for the patient P in the operative environment.

Loop 500 includes the following components interconnected: diversion section tubing 521 connected between the patient's blood vessel (not shown) and valve 532, diversion section tubing 522 between the valve 532 and flow through cell 510, return section tubing 523 between the flow through cell 510 and valve 534, return section tubing 524 between valves 534 and 536, return section tubing 525 between valve 536 and another blood vessel (not shown) of the patient P, and a bypass tubing section 526 between valves 532 and 536.

The tubing, generally 520, and the valves, generally 530, must be made from materials which are biocompatible with the patient's biological fluid and strong enough to withstand use of flowing pressurized fluid therethrough. A leak in the loop 500 could be traumatic for the patient P.

Preferred commercially available materials for the tubing 520 are "TYGON" brand plastic tubing available from Norton Performance Plactics of Akron, Ohio.

Preferred commercially available valves are three-way stopcock type valves marketed under the trademark "INTRALOK" from Abbott Sorenson Research of Salt Lake City, Utah.

The flow through cell 510 must be made of a transparent material used in spectrophotometric instrumentation, such as quartz plate glass, and geometrically configured and constructed in a manner to minimize the stagnation of the biological fluid in that portion of the cell irradiated with the near infrared light. Glassblowers skilled in the art are capable of configuring the cell 510, which preferably has an oval shape with opposing ports at the perimeters of sharper curvatures.

The loop 500 has a biological fluid flow in the direction of arrow F1 from the patient P through diversion section comprising tubing 521 and 522 and in the direction of arrow F2 to the patient through tubing 523, 524, and 525.

Manipulation of valves 532 and 536 allow the control of the amount of biological fluid flowing through cell 510. It is desired that adequate biological fluid flow through cell 510 during spectral detection. However, if it is desired to entirely bypass cell 510, valves 532 and 536 may be opened in a way to direct all fluid flow through section 526.

Valve 534 is adjacent the emergence of the tubing 523 from the cell 510 in order that any independent quantification needed or desired may be performed in the loop as closely as possible to the location of the spectral irradiation and detection in the cell 510.

Use of loop 500 may be combined with any spectrometric instrumentation described above, although the use of a spectrometer such as a Model 6250 spectrometer, with a computer such as a personal computer, described above is preferred.

Further, the spectra data may be gathered in conjunction with an extracorporeal blood gas sensor (EBGS) sold by Cardiovascular Devices, Inc. of Irvine, Calif.

Through the use of real time monitoring of the spectral data and use of the mathematical correlation obtained according to the methods of the present invention, hematocrit or hemoglobin concentration may be monitored nearly instantaneously, permitting the health care practitioner to treat the patient without delay.

The extracorporeal loop 500 may be used in routine dialysis procedures as part of the dialysis blood loop to monitor the water content of the blood and other properties of interest. Another use of the extracorporeal loop 500 is in critical cases of prematurely born babies, neonatals, that require the use of ExtraCorporeal Membrane Oxygenators (ECMO) wherein a blood loop is formed with the ECMO to oxygenate the blood for days, if needed, until the proper maturation of lung functions is attained. It is a critical setting, and continuous monitoring of the blood components such as hemoglobin concentration and hematocrit among other properties, can be vital. Further, the use of loop 500 in the ECMO eliminates the undesirable need to withdraw blood samples for these analyses from the neonatal infant already in critical condition.

During the experiments recited in the examples below, it was found that approximately a 15 minute time difference exists in a mammal before any change in the concentration of oxyhemoglobin was observed after the oxygenation has been changed during the operative period. It was also noted in those experiments that approximately 3 to 4 minutes thereafter were required to complete the change of oxygenation level. Thus, nearly 20 minutes exists between the time the change in oxygenation is commenced and the oxygenation has stabilized. Current operative therapeutic monitoring involves the withdrawal of blood samples from the patient and the delivery of those samples to a remote location for static condition analysis. By the time the sample is analyzed the next stage of oxygen change may commence, thereby requiring constant withdrawal of blood samples and repeated analyses in the static condition, which delays the efforts to monitor the true hemoglobin concentration and the state of its oxygenation.

Use of a flow through cell 510 or an extracorporeal blood gas sensor with a cell 510 permits real time monitoring of the time taken to commence and complete the oxygenation change as well as maintaining in real time a monitor of the patient's condition for properties of interest such as hematocrit, hemoglobin concentration, and percent oxygen saturation.

Without being limited thereto or thereby, the following examples illustrate the methods of the present invention used to predict hematocrit and hemoglobin in whole blood in a dynamic condition using an extracorporeal blood loop.

EXPERIMENTAL PROCEDURE FOR EXAMPLES

On two separate occasions, a number of whole blood spectra of canines were observed in an extracorporeal blood loop having the assembly of components depicted in FIG. 14 and described immediately above. During the course of the gathering of such spectra a number of whole blood samples were withdrawn from such canines for independent quantification of the hemoglobin concentration through the use of an "IL482" co-oximeter available from Instrumentation Laboratories or an "ABL2" blood gas analyzer available from Radiometer of Copenhagen, Denmark and independent quantification of the hematocrit by centrifuging. Also, a blank reference spectrum was obtained using an air filled cell. The diffusely transmitted light was gathered after traveling through each sample in the flow through cell 510 described above and also depicted in FIG. 1 as item 113.

All of the measurements were taken at canine body temperature, which fluctuated randomly during the spectra gathering over a range of about ±three degrees C. or less.

Specifically, an extracorporeal blood loop was established for both of the individual sessions: the spectra set A was gathered using a 11 Kg female Beagle dog approximately two years old; and the spectra set B was gathered using a 11 Kg. female Beagle dog approximately four and one half years old. While there were some minor variations during the experimentation, the experiments used the following protocol with the following materials, instruments, and supplies.

The materials and instrumentation used for the experiment are identified by reference letters schematically in FIG. 14 and were the following:

A respirator, R, made by Bird Corporation of Palm Springs, Calif. coupled to a semi-open anaesthesia system made by Fortec/Cyprane of Keighley, Yorkshire England connected to various pure gases such as oxygen and a mixture of 5 percent oxygen in nitrogen made by Union Carbide, Linde Division of Danbury, Conn. sold under the trademark "MEDIBLEND™" gases;

Heated water blankets, B, "Model K20" sold by American Pharmaseal Company, American Hospital Supply Corporation, Valencia, Calif.; "THINSULATE®" brand thermal blankets, B, made by Minnesota Mining and Manufacturing Company;

A "BURDICK" CS525 EKG-Blood Pressure Monitor, M, with a blood pressure transducer connected thereto, made by Burdick Corporation of Milton, Wis.;

EKG Pregelled Electrodes #2256 made by Minnesota Mining and Manufacturing Company; cannulae, 2¼" long, 14 gauge made of polytetrafluoroethylene and sold under the trademark "JELCO™" made by Jelco Labs, Rariton, N.J.;

Needle thermometers connected to a LED readout temperature monitor, T, available as "YSI-400" brand monitor made by Yellow Springs Instruments Company, Inc. of Yellow Springs, Ohio;

The blood loop 500 comprising "TYGON®" tubing, generally 520, having a 1.587 mm wall and a 3.175 mm internal diameter made by Norton Performance Plastics of Akron, Ohio; three-way stopcock valves, generally 530, sold under the trademark "INTRALOK®" made by Abbott Sorenson Research of Salt Lake City, Utah, a flow through cell 510 of approximately 1.6 mm path length made of quartz-plate glass made at Minnesota Mining and Manufacturing Company for this experiment;

A Model 6250 Pacific Scientific Infrared Spectrometer, S, having the structure described with reference to FIG. 1 and operating in wavelength ranges from 680 nm to 1235 nm;

An IBM PS/2 Personal Computer, C, available from IBM Corporation of Boca Raton, Fla.;

A micropipette centrifuge, MC, made by Heraeu Sepatech GmbH of West Germany and distributed in the United States by American Scientific Products of Minneapolis, Minn.;

An Instrumentation Laboratories "IL-482" co-oximeter, O, made by Instrumentation Laboratories of Lexington, Mass.;

A "BECKMAN GPR" refrigerated centrifuge, RC, made by Beckman Instruments;

An electro-surgical generator, ES, "Model 600" electro-surgical unit made by Minnesota Mining and Manufacturing Company or "MODEL 9900" electrosurgical unit available from Concept Incorporated of Clearwater, Fla. with a scalpel and dispersive plate system using "SCOTCHPLATE" 1145 dispersive plate and electically conductive gel "#1103", both available from Minnesota Mining and Manufacturing Company;

A "ABL-2" Blood Gas Analyzer, BG, made by Radiometer of Copenhagen, Denmark, represented in the United States by Radiometer America Inc. of West Lake, Ohio; and A number of hand-held, test strip blood drop glucose testers commercially available under the name "GLUCOSTIX®" made by Miles Laboratories of Elkhart, Ind..

Medical and surgical supplies used for the experiment are as follows:

Lactated Ringers Solution, L, for injection, USP, 1,000 ml made by Abbott Laboratories, North Chicago, Ill.;

0.9 percent NaCl injection, USP 1,000 ml bag, N, made by Abbott Laboratories, North Chicago, Ill.;

"ISOFLURANE-AERRANE®" anaesthesia agent made by Anaquest of Madison, Wis.;

"LYPHOMED" heparin sodium 1000 units per ml anticoagulant commercially available from Lyphomed Inc. of Rosemount, Ill.;

Acepromazine maleate commercially available under the name "ACE®, AVECO™" from Ayerst Laboratory Inc of New York, N.Y. in 10 mg per ml dosages;

Atropine Sulfate Injection, 1/120 grain commercially available from Anpro Corp of Arcadia, Calif.;

"BIO-TAL" thiamylal sodium, USP injection available from Bioceutric Division, Boehringer Ingelheim Animal Care Inc. of St. Joseph, Mo.;

and various commonly available and used supplies such as sutures and the like.

The method of the experiment was as follows: the Beagle dog was first administered by subcutaneous injection 0.05 mg/Kg of the sedative Acepromazine and then 0.025 mg/Kg of Atropine. Anaesthesia was induced by the administration of the barbituate Bio-tal (4%) to obtain the desired level of anaesthesia which was then sustained by the intubation of the trachea and maintained with a mixture of isoflurane in pure oxygen from the respirator, R.

The skin was shaved on the medial aspects of the hind legs and the neck for placement of the cannulae and the animal was transferred from initial preparation areas to the operating room.

A jugular vein cut-down at the shaved neck area was performed and the teflon cannula was inserted and connected to a drip bag containing the lactated Ringers Solution, L, dripping at the rate of 2 to 5 ml per pound per hour. The anaesthesia was maintained by continued delivery of isoflurane at 1–2 percent delivered in pure oxygen via the semi-open anaesthesia system. Three EKG electrodes were attached on the thorax of the animal at appropriate diagnostic locations and connected via cables to the Burdick CS525 EKG-Blood Pressure Monitor, M.

A "SCOTCHPLATE®" 1145 Electro-surgical plate (not shown in FIG. 12) was placed under the animal on the back with an electrically conductive paste (Gel #1103 available from Minnesota Mining and Manufacturing Company) between the plate and the skin. An electro-surgical scalpel, (not shown in FIG. 12) was attached to an electro-surgical unit (ESU) generator, ES, and used to make a skin incision over the proximal medial femur with dissection carried down to expose the femoral artery and vein. Fourteen gauge "TEFLON™" cannulae were inserted into the femoral artery and vein, respectively, and tied in place with a 2-0 vinyl suture. Next, the contra-lateral femoral artery similarly exposed and a 14 gauge cannulae was inserted and similarly secured with suture. This latter cannulae was connected to the Burdick Corporation blood pressure transducer, M, and connected via hydraulic lines to a pressurized bag containing 0.9 percent sodium chloride solution dripping at approximately 3 ml per hour to prevent any clogging of the cannula.

Heated water blankets, HB, with "THINSULATE®" blankets, B, were placed under and over the animal to help maintain body temperature at the initial temperature of 34.8° C. as measured by inserting the needle thermometer near the site of the contra-lateral femoral artery to indicate the core body temperature in the intestinal area. The thermometer readings were displayed on the "YSI-400" Readout Temperature Monitor, T. A second channel of that monitor was connected to a thermometer needle inserted into the tubing section 523 at the outlet port of the blood flow through cell 510 to monitor the temperature of the blood in the extracorporeal loop 500. The "TYGON®" tubing was assembled in lengths from about 30 cm to 50 cm. One stop cock valve, 532, was placed in the diversion section of the loop between tubing 521 and 522. A second stop cock valve, 536, was placed in the return section of the loop between tubing 524 and 525. Between the two valves, 532 and 536, a piece of tubing 526 was connected to provide a bypass, which by manipulation of the two valves, 532 and 536, could eliminate flow of the blood through the flow through cell 510 entirely, or to control the rate of flow therethrough.

A third stopcock valve, 534, was placed in the return section of the extracorporeal blood loop 500 between tubing 523 and 524 to permit withdrawal of samples periodically for testing of various blood related parameters using the centrifuge, MC, the co-oximeter, O, the blood gas analyzer, BG, and the glucose test strips. The flow through cell 510 was connected to the opposing ends of the diversion section at tubing 522 and the return section at tubing 523 and placed within the Model 6250 Spectrometer.

Initially the cell 510 and associated tubing 520 was filled with a 0.9% NaCl solution made by Abbott Laboratories of North Chicago, Ill. in order to remove air from the cell 510 and tubing 520 to avoid injection of air emboli upon connection of the extracorporeal loop 500 to the animal and to allow recording of a spectra of water so that known features of the water may serve as a reference of the proper functioning of the loop 500 and spectrophotometric system depicted in FIG. 1. The flow through cell 510 was approximately 6 cm long and 3.5 cm wide at the middle of the cell and mounted onto a transport metal plate of the dimensions of 11 cm by 6 cm with a circular aperture of approximately 1.5 cm. The plate was inserted into the positioning tracks of the chamber and the Model 6250 Spectrometer, S. The chamber cover was shut and taped to prevent accidental opening during the experiment.

The computer control of the cell transport mechanism was disabled by disconnecting the transport board cable between the PS/2 Personal Computer, C and the Model 6250 Spectrometer, S. This was done to prevent movement of the cell 510.

To further prevent any aberrations of the spectrometer, S, receiving incident light, the tubing 522 of the loop 500 leading to and the tubing 523 coming from the Model 6250 Spectrometer, S, was wrapped with black vinyl electrical tape available from Minnesota Mining and Manufacturing Company. Thus, the tubing itself was prevented from acting as a light guide which upon entering the cell would serve as a noise source of light.

Next, the animal was injected with 3800 units of sodium heparin from a 1,000 unit/ml solution available under the brand name "LYPHOMED". The heparin served as a blood anticoagulant because the blood in the extracorporeal loop would be in contact with various materials such as the "TEFLON™" cannulae, valves 530, tubing 520, and the flow through cell 510.

Next the reference spectrum with air in the cell was taken and stored. Then, the loop 500 was filled with saline, making sure all trapped air bubbles were removed and then connected to patient, P.

The diversion section tubing 522 was connected to the inlet port of the cell 510 so that any spurious air bubbles would be flushed from the cell 510. Next, the extracorporeal loop 500 was adjusted at valves 532 and 536 to permit the animal's blood to flow from the animal through the flow through cell 510 and back to the animal, avoiding the bypass tubing 526 between the diversion section valve 532 and the return section 536 which would eliminate blood flow through the flow through cell 510.

After allowing the blood to flow through the cell 510 for approximately 10 minutes, a 1 ml sample of blood in a 1 ml syringe was withdrawn through valve 534 and subjected to blood gas analysis and co-oximetry and centrifuging. Less than 10 seconds after the withdrawal of the blood sample, 64 scans of spectra were acquired by the spectrometer upon initiation from the personal computer. Approximately 24 seconds were required to obtain these spectra.

Strict adherence to the protocol of blood sample handling is required to minimize aberrations. For example, blood is withdrawn into new syringes for every sample. The operation of the valve 534 where the blood is withdrawn must be such that only blood exiting the flow through cell 510 fills the syringe in order to avoid any blood which has proceeded further in the direction of the return to the animal has not been also withdrawn. A first one-third to one-half ml of withdrawn blood is reinjected into valve 534 positioned to direct such reinjected blood into section 524 and towards the animal. This procedure helps to force any old blood and/or air in the valve from being also withdrawn. The next one ml of blood withdrawn in the syringe is removed for analysis by instruments, O, MC, and BG. Further, the blood from the syringe is injected into all three of the diagnostic analyzers, O, BG, and MC as soon as possible, within less than a minute, in order to obtain accurate readings not affected by atmospheric changes to the samples.

While the animal was on 100 percent inspired oxygen and confirmed by the samples analysis, the gas was changed to a mixture of 5 percent oxygen in nitrogen. After approximately 9 minutes, another blood gas analysis was performed by withdrawal of a blood sample through valve 534 and placement in the diagnostic analytical equipment described above.

Although the percentage oxygen fell from 642 to 507 mm of Hg, the oxygen saturation of the hemoglobin was unchanged at 99.5 percent. It has been found that oxygen saturation decreases significantly only when the percentage oxygen falls below approximately 100 mm of Hg. Because of the time delay from the change in oxygen inspiration until the oxygen saturation had stabilized, the next blood gas analysis was not taken until approximately 22 minutes That analysis showed $PO_2$ of 53.3 mm of Hg and $O_2$ saturation of 93.8 percent.

Twenty-six minutes after changing the gas to 5 percent oxygen, the blood gas analysis showed an oxygen saturation of 68.6 percent with a corresponding $PO_2$ of 27.8 mm of Hg. Immediately after each blood gas analysis, the 64 spectra were recorded by the spectrometer, S, by initiation from the personal computer keyboard, C.

Next, using two 60 ml syringes, 100 ml of blood were withdrawn slowly from the valve 534 on the return section of the blood loop. To assure life sustaining blood pressure, the blood pressure EKG monitor, M, was closely watched and the drip flow rate of the lactated Ringer solution, L, was increased for a few minutes to at least one drop a second to bring back or otherwise sustain blood pressure if it drops significantly from the original values recorded, 102/58 mm of Hg.

The 100 ml of blood withdrawn was centrifuged at 3000 RPM for 10 minutes in 2 centrifuge tubes of equal volumes and weights in a "BECKMAN GPR" refrigerated centrifuge, RC, utilizing a "GH-3.7" rotor available as catalog #349702 from Beckman Instrument, Inc. of Palo Alto, Calif.. The plasma supernatent fraction was removed with a pipette from each tube and the densely packed red blood cells in the lower portion of the centrifuge tubes were stored in the refrigerator at approximately 4° C.

The plasma was returned to the animal through the same valve 534 to maintain plasma volume but with a reduced hematocrit and hemoglobin concentration.

The procedure of withdrawing 100 ml of blood, centrifuging it, re-injecting the plasma and storing the red blood cells in the refrigerator was repeated several times. Each time, the blood gas analysis was performed and the spectra taken both before and after each such procedure. The hematocrit varied for each animal, e.g. for one animal from an initial percent of about 47 percent to a low of about 22 percent, at which point the refrigerated red blood cells were re-injected into the animal through the valve in the return section of the loop to increase the hematocrit to its original level and to restore the hemoglobin concentration. Spectra were taken before and after the red blood cell re-injection into the loop and contributed to the spectra used for the training set spectra from which the mathematical regression techniques after pre-processing established the mathematical correlation between the hemoglobin concentration or hematocrit and the water content of the blood.

EXAMPLES 1–6

SECOND DERIVATIVE PRE-PROCESSING TECHNIQUE

EXAMPLE 1

The two experimental sessions were conducted according to the experimental procedure described above. Table I below identifies the sessions as sets A and B, and the number of samples analyzed are identified as the number of spectra obtained, which varied as shown. A representative group of samples from set A are graphed in FIG. 4. The sample spectra indicated the ranges of variability of the spectral data found, against which mathematical correlations would have been otherwise attempted to be calculated.

Through the use of centrifuging with centrifuge, MC, the hematocrit (Hct) found for both sets is expressed in Table I below as a range which varied from as low as 22 percent to as high as 47 percent. Similarly, the hemoglobin concentration (Hb) range in both sets was determined by cell lysing in the IL482 co-oximeter, O. The range for the sets was from about 8.0 to about 16.6 grams per deciliter (g/dL). Finally the percent oxygen saturation range ($O_2$ Sat.) in both sets was determined using the co-oximeter, O. The range for the sets was from 61 percent to 100 percent. Within each set, individual samples having oxygen saturation greater than 95 percent were segregated and assigned to a subset, A1 and B1, respectively, to distinguish the methods of the present invention between samples of nearly fully oxygenated conditions and conditions where oxygen saturation varied considerably.

Table I below further identifies the correlation of hematocrit to hemoglobin which demonstrated correlation for the spectra observed greater than 0.99 for both sets.

TABLE I

Sets of Samples Spectrally Analyzed and Independent Quantification Ranges of Hematocrit, Hemoglobin and Oxygen Saturation

| Set | No. of Spectra | Hct Range (%) | Hb Range (g/dL) | Hct/Hb Corr. | $O_2$ Sat. Range (%) |
|---|---|---|---|---|---|
| A | 19 | 22–47 | 8.0–16.6 | 0.999 | 67.0–100.3 |
| A1 | 14 | 22–47 | 8.2–10.7 | | 99.2–100.3 |
| B | 8 | 24–32 | 8.2–10.8 | 0.995 | 61.2–99.8 |
| B1 | 6 | 24–31 | 8.0–10.7 | | 98.5–99.8 |

With the spectra detected, involving both the measurement of the diffuse transmission spectra and the transformation of that spectra to absorbance spectra, the analysis described in FIG. 2 and FIG. 3 was performed, using the second derivative transformation pre-processing technique and the ratio pre-processing technique, respectively, for the analysis of both hematocrit and hemoglobin.

While a total of 27 individual spectral detections were obtained in two sets for this example, from two individual canines, generally, it is possible to develop a training set and independent quantification training set spectral data from as few as 25 samples to as many as an infinite number of samples. When spectra in Sets A and B having greater than 95 percent oxygen saturation were segregated into Sets A1 and B1, respectively, 20 spectra were used in some of the following examples together or separately to form the training set or to validate the method. However, based on other work of some of the applicants, such as that disclosed in U.S. patent application Ser. No. 07/408,747 (File Number UOFW-1-4265) and U.S. patent application Ser. No. 07/408,746 (File Number 44446USA8A) of the suitability of the techniques in other applications, for these purposes, the use of 20 spectra was deemed sufficient as proof of the propriety of the method of the present invention even though a more robust sampling is preferred.

The purpose of establishing a training set for comparisons and prediction purposes is to attempt to anticipate sampling differences which may exist in various individuals at various times. In other words, the training set should be as broad as possible to include as many variances within each of the factors affecting the measurement of the property of interest.

Ideally, the training set includes samples that represent all of the different kinds of changes in the hematocrit and hemoglobin concentration over a full range of values likely to be encountered in an unknown sample as well as all of the other kinds of changes within each factor likely to affect blood sampling, e.g., temperature, amount of liquids, details of light scattering, presence of other components, and physiological condition of the patient.

Notwithstanding such ranges of hematocrit and hemoglobin in these sets, it is seen that the correlation between hematocrit and hemoglobin is quite precise, greater over 0.99 in both sets.

Having established both training sets A and B and independently quantifying the hematocrit and hemoglobin ranges within each of those sets, the mathematical analysis depicted in FIG. 2 was performed.

First, the second derivative pre-processing technique was performed against the combination of the sets using the Near Infrared Spectral Analysis software program described above, with a personal computer described above, and available with the Model 6250 spectrometer from Near Infrared Systems to compute the second derivatives, to perform the linear regression, to select the best wavelength, and to save the regression coefficients (steps 124, 125, 127, 128, and 131 of FIG. 2). Other software, "VAX IDL Interactive Data Language" available from Research Systems, Inc. (copyright 1982–1988) was used to apply the regression model, predict the property, (steps 132 and 133 of FIG. 2) and to compute the SEC, SEP, and the bias for validation purposes. In these Examples the approximated second derivative spectra obtained was based on the use of segment of 20 datapoints or 15.8 nm and a gap of 0 datapoints. Thus, each point for purposes of calculating the second derivative was a band 15.8 nm wide without any gap between the bands.

Figure 4:
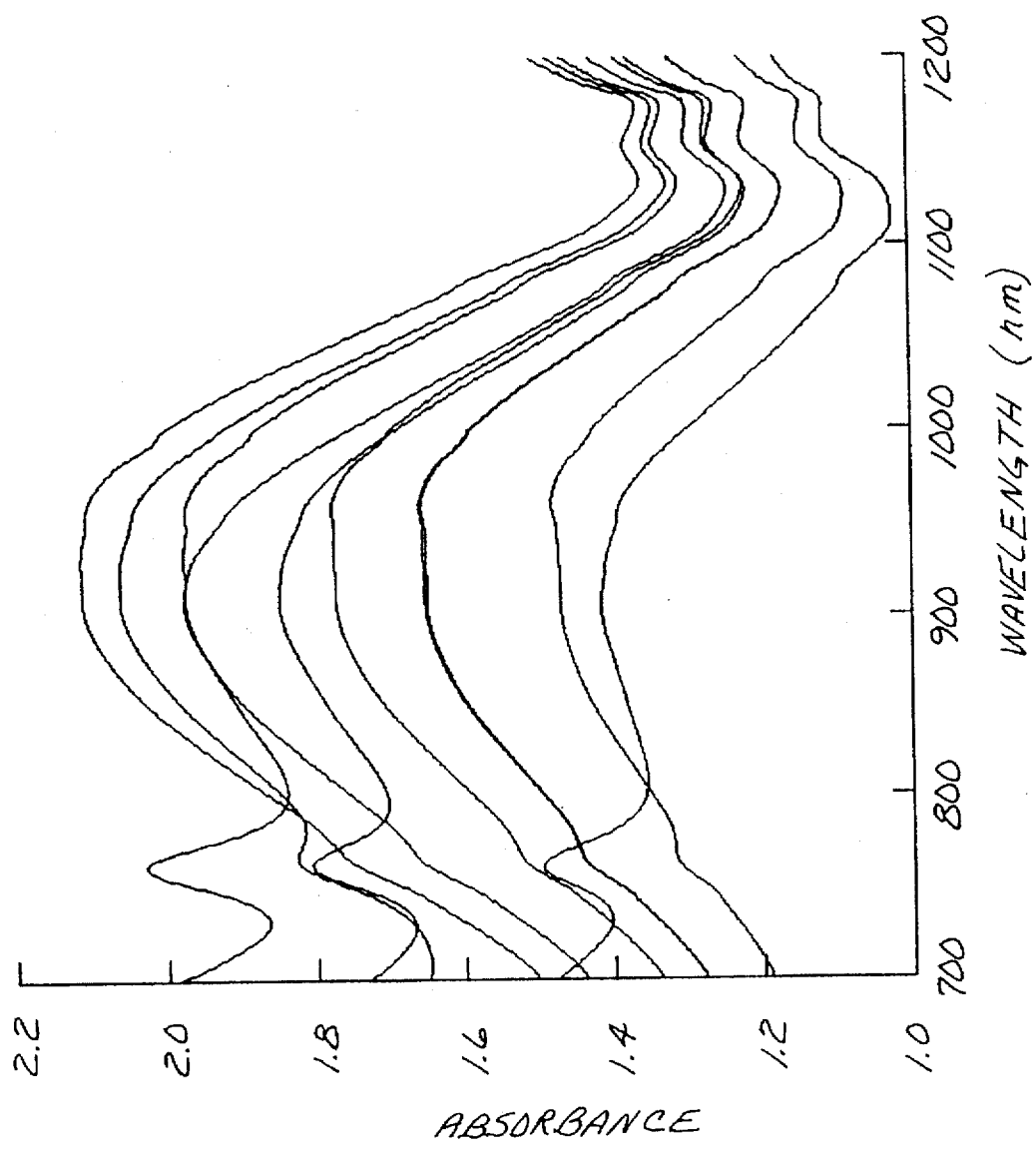
FIG. 4 is a graphic representation of typical whole blood spectra detected in a dynamic condition indicating the effects of typical light scattering variances and other instrumental noise variances.
Figure 5:
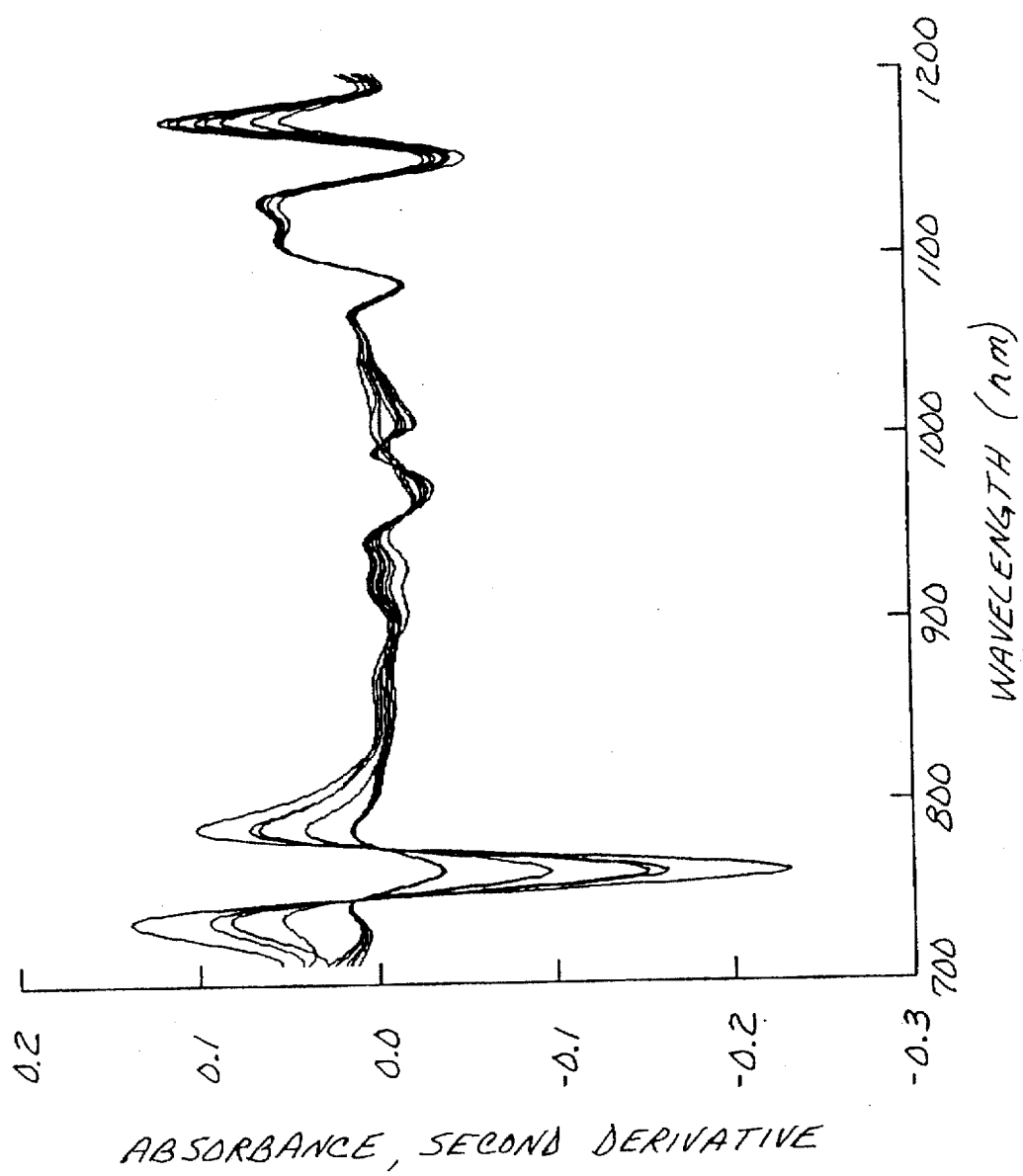
FIG. 5 is a graphic representation of the same whole blood spectra as in FIG. 4 after the application of the multiple derivative transformation to minimize the effects of typical light scattering variances and other instrumental noise variances.

The group of spectra for Set A are shown in FIG. 4 are re-depicted in FIG. 5 after the second derivative pre-processing has been performed. As may be readily seen, the variations in absorbances as caused by baseline offsets and other variances from spectrum to spectrum are minimized, permitting better attempted mathematical correlation.

The second derivative pre-processing technique computes a transformed absorbance value for all of the wavelengths in order to find the best correlation in the area of the water absorbance peak.

For the analysis of hemoglobin, Sets A and B were combined, comprising 27 spectra. Using second derivative transformation as the pre-processing technique, the mathematical analysis depicted in FIG. 2 was performed and yielded a wavelength of 892 nm with a multiple correlation coefficient (R) of 0.991 and a standard error of calibration (SEC) of 0.39 g/dL. However, this wavelength is within a region of the spectrum where a broad absorbance peak of hemoglobin exists and which peak is dependent upon on the percent oxygen saturation. Further use of a wavelength chosen from a set of spectra which is near the minimum number of spectra desired for a versatile training set can be rejected because the smaller training set can invert the priority of correlation of the various wavelengths to the actual value determined by independent quantification.

Another reason for rejection of a wavelength in the 900 nm region of broad hemoglobin absorbance is the possible interference by other forms of hemoglobin absorbing in this region, such as methemoglobin.

Figure 6:
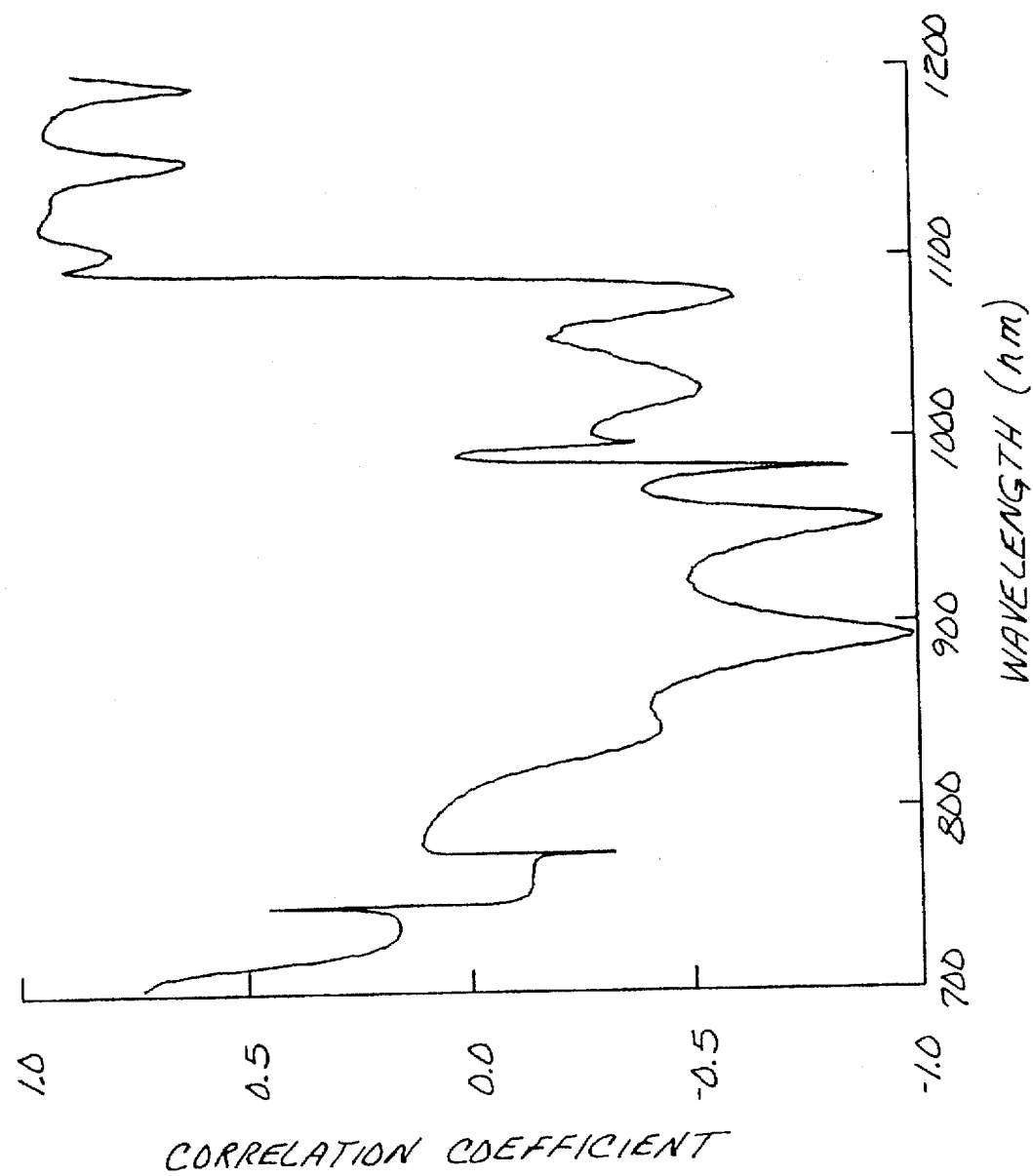
FIG. 6 is a correlation plot of correlation coefficient versus wavelength for hemoglobin after the spectral data were second derivative pre-processed and regression analysis of the spectral data was performed against hemoglobin.

Therefore, to find a wavelength which did not exist in a region substantially affected by the spectra of the various forms of hemoglobin, a correlation plot was generated, using the Near Infrared Spectral Analysis software described above or the "VAX IDL, Interactive Data Language" described above. FIG. 6 depicts that correlation plot. As seen in FIG. 6, the correlation in the region of 890 nm is an anomalously sharp band where variations in the wavelength selected can significantly reduce the extent of correlation. Conversely, the correlation in the region of 1150 to 1190 nm is a broader band where variations in the wavelength selected do no significantly reduce the extent of correlation. As discussed below, predictions using a wavelength within this range are acceptable.

From that plot, it was found that in the range of 1150 to 1190 nm corresponding to the broad absorbance peak of the water content, use of a wavelength within the range of 1160-1175 nm, specifically, 1170 nm, had acceptable correlation for generating a calibration equation. The results of the mathematical analysis computed from using the Near Infrared Spectral Analysis software described above and the VAX IDL software described above in the same manner as described earlier in this Example using 1170 nm yielded a R=0.9064, and SEC=1.20 g/dL. The slope was 126.3, and the intercept was 3.132. Thus, in this instance, the linear functional equation using a single independent variable was:

Concentration of Hemoglobin=3.13+126.32*(Second Derivative of Spectral Intensity at Wavelength 1170 nm)

By choosing to concentrate on the water absorbance peak around 1150 to 1190 nm, and particularly around 1160 to 1175 nm where there is far less absorbance of either form of hemoglobin than in the region of 925 nm, the mathematical correlations achieved were deemed more acceptable because the correlation was more resistant to errors caused by variations in percent oxygen saturation, and as seen below, SEP and bias were acceptable. Thus, applying the multiple derivative transformation pre-processing technique, variability is minimized when using a wavelength corresponding to the absorbance of the water content in whole blood.

EXAMPLE 2

To validate the performance of the correlation model at about 1170 nm, the combined sets A+B were then used as a known set to predict sets A, A1, B and B1, as if such were unknown. The Near Infrared Spectral Analysis software was used to generate the model combining Sets A and B, and the VAX IDL software was used to compute the results. Table II shows the results found.

TABLE II

Prediction of Individual Sets Against Combined Set A + B For Hemoglobin at 1170 nm After Second Derivative Pre-Processing

| Set | R | SEC g/dL | Bias g/dL |
|---|---|---|---|
| A1 | 0.995 | 0.84 | 0.56 |
| A | 0.930 | 1.13 | 0.03 |
| B1 | 0.993 | 0.72 | 0.57 |
| B | 0.456 | 1.31 | −0.07 |

The distinctions between the prediction of sets A and B compared with sets A1 and B1 were multiple. The prediction performed well using sets A1 and B1 when the percent oxygen saturation was measured as greater than 95 percent. Correlation R was more precise with the segregated sets A1 and B1, and SEC's were less than 1.0 g/dL. However, the five spectra of set A not found in set A1 and the two spectra of set B not found in set B1 lowered the R and raised the SEC, indicating a less precise prediction achieved. Further, the bias trended more negatively as the lower percent oxygen saturation spectra were included in the set predicted, indicating the lower percent oxygen saturation spectra individually were predicted consistently lower than the higher percent oxygen saturation spectra.

While the use of the second derivative pre-processing technique at the spectral intensity of around 1170 nm wavelength is acceptable for certain instances in a dynamic condition, the acceptability is more apparent under conditions where the percent oxygen saturation is greater than 95 percent.

EXAMPLE 3

The validation of the performance of the selected linear functional equation described in Example 1 was performed to assess standard error of prediction (SEP) and bias. Each set was used as a known and used to predict each other set as if such other set were unknown. The Near Infrared Spectral Analysis software and the VAX IDL software were used in the same manner as described in Example 1 and used in Example 2 to compute the results. Table III shows the results found.

TABLE III

Prediction of Individual Sets Against Other Individual Sets For Hemoglobin at 1170 nm After Second Derivative Pre-Processing

| Known Set | R | SEC g/dL | Slope | Intercept | Unknown Set | SEP g/dL | Bias g/dL |
|---|---|---|---|---|---|---|---|
| A1 | 0.995 | 0.29 | 155.7 | 0.35 | B1 | 0.64 | −0.50 |
|  |  |  |  |  | B | 2.06 | −1.24 |
| A | 0.922 | 1.18 | 136.2 | 2.39 | B1 | 0.50 | 0.39 |
|  |  |  |  |  | B | 1.40 | −0.29 |
| B1 | 0.992 | 0.16 | 142.5 | 1.63 | A1 | 0.47 | 0.20 |
|  |  |  |  |  | A | 1.18 | −0.35 |
| B | 0.406 | 1.05 | 43.5 | 7.48 | A1 | 2.31 | −1.13 |
|  |  |  |  |  | A | 2.62 | −1.49 |

The same trends found in Table II were more accentuated in the results shown in Table III. The prediction using one segregated set A1 against another, B1, and vice versa demonstrated the precision of the linear functional equation within an acceptable range. The prediction using full set A against full set B, and vice versa, was less acceptable without possible further adjustment using another independent variable such as percent oxygen saturation. The prediction of a segregated set against a full set, e.g., using A1 to predict B, compared with using a full set to predict a segregated set, e.g., using A to predict B1, demonstrated the desirability of having a broadly based known training set. The breadth of the training set must be adequately balanced among spectra of various types. Only two spectra of eight spectra in set B were not present in set B1. Yet those two spectra were so different due to percent oxygen saturation as to effect greatly the R, SEC, SEP, and bias. However, the five of nineteen spectra missing from set A in set A1 did not cause comparable lack of prediction precision. Therefore, planning great variations in the construction of the training set with balance among the variations will provide the better results for precise prediction.

The bias results in Table III demonstrated accuracy of the linear functional equation, when considering known sets A1, B1 and A. Yet the trend in each instance of prediction where the unknown set included spectra having lower percent oxygen saturation was more negative, indicating an under-prediction of the property of interest.

EXAMPLE 4

The same experiments as those described in Examples 1–3 were conducted for the analysis of hematocrit using the second derivative transformation pre-processing technique computed using the Near Infrared Spectral Analysis software and the VAX IDL software in the same manner as described in Examples 1–3. The combined sets A and B were analyzed for the best wavelength not likely to be rendered inaccurate by changes in concentration of the various forms of hemoglobin, i.e., in the range of 1150–1190 nm. The combined sets having 27 individual spectra, yielded acceptable results.

As in the case of the hemoglobin of Example 1, the wavelength initially selected by the mathematical analysis was around 892 nm, (R=0.987 and SEC=1.28%) in the region of a broad hemoglobin absorbance peak. Therefore, using a correlation plot generated in the same manner as that for Example 1, it was determined that use of a wavelength in the region of 1150–1190 would provide acceptable results. The wavelength between 1160 and 1175 nm was chosen, 1169 nm, and provided the following results: R=0.899 and SEC=3.47% with a slope of 356.17 and an intercept of 10.19.

The combined set A+B was then used as a known set and the individual sets A1, A, B1, and B were predicted therefrom to assess standard error of calibration. The results are shown in Table IV.

TABLE IV

Predict Individual Sets Against the Combined Set For Hematocrit at 1169 nm After Second Derivative Pre-Processing

| Set | R | SEC (%) | Bias (%) |
|---|---|---|---|
| A1 | 0.996 | 2.56 | 1.75 |
| A | 0.934 | 3.21 | 0.27 |
| B1 | 0.984 | 1.77 | 1.29 |
| B | 0.404 | 3.99 | −0.64 |

As seen in Table IV, sets A1 and B1 were more precise than sets A and B. The change in bias from smaller sets A1 and B1 to sets A and B, respectively, was more negative, again indicating the trend in accuracy of the linear functional equation to under-predict spectra having lower percent oxygen saturation.

The individual sets A1, A, B1, and B were treated as known sets and the other sets were treated as unknown sets to assess standard error of prediction and bias. Table V shows the results obtained.

TABLE V

Predict Individual Sets Against Other Individual Sets For Hematocrit at 1169 nm After Second Derivative Pre-Processing

| Known Set | R | SEC (%) | Slope | Intercept | Unknown Set | SEP (%) | Bias (%) |
|---|---|---|---|---|---|---|---|
| A1 | 0.996 | 0.73 | 450.0 | 1.71 | B1 | 2.54 | −1.99 |
|  |  |  |  |  | B | 6.62 | −4.21 |
| A | 0.926 | 3.29 | 395.3 | 7.22 | B1 | 0.89 | 0.47 |
|  |  |  |  |  | B | 4.52 | −1.58 |
| B1 | 0.956 | 0.63 | 420.1 | 5.54 | A1 | 1.79 | 1.38 |
|  |  |  |  |  | A | 3.14 | −0.21 |
| B | 0.362 | 3.21 | 117.0 | 22.43 | A1 | 6.42 | −2.54 |
|  |  |  |  |  | A | 7.22 | −3.52 |

As seen in comparison with the results shown in Table III, the same or similar trends were found for hematocrit as found for hemoglobin concentration. Segregated sets A1 and B1 provided the more precise predictions, but the larger set A having a better balance of percent oxygen saturation spectra variations predicted set B1 with acceptable precision. The prediction by set B and the prediction of set B showed the effects that two outlier spectra can have on a smaller set having less robustness of spectra.

Bias for the predictions by all of the sets were more positive when predicting the segregated sets A1 or B1 than when predicting the full sets A or B, again indicating an under-prediction is possible when the spectra has a lower percent oxygen saturation.

FIG. 8 is a graph of the comparison of predictions of set A to the actual independently quantified values for hematocrit.

EXAMPLE 5

Thus, it was determined that in the dynamic condition of whole animal blood, better results were obtained consistently when the model was confined to occasions when the samples being analyzed had greater than about 95 percent oxygen saturation. While that condition exists in the great majority of patient diagnostic circumstances, there are many occasions when the patient may have less than 95 percent oxygen saturation. For humans, that is known to be in circumstances when the partial pressure of oxygen in the patient is less than about 60 mm of Hg.

Therefore, as an optional methodology, the percent oxygen saturation of the patient was added as an independent variable to the linear functional equation and multiple linear regression analysis or the like was performed as depicted in FIG. 10 in the case of multiple derivative transformation pre-processing. With two animals studied, the percent oxygen saturation was measured for each spectrum using the "IL-482" co-oximeter. That data comprised one column of data used in replacement of one column of spectral data to achieve a multiple variable set of data, which the Near Infrared Spectral Analysis software and the VAX IDL software computed in the manner described in Examples 1–3 to yield the mathematical results.

Table VI shows the results found when individual sets were used to predict other individual sets for hemoglobin where the percent oxygen saturation was added to the mathematical analysis as an independent variable. Table VII shows the analogous results for hematocrit.

TABLE VI

Prediction of Individual Sets Against
Other Individual Sets With Adjustment For
Percent Oxygen Saturation From A Co-Oximeter
For Hemoglobin at 1170 nm After
Second Derivative Pre-Processing

| Known Set | R | SEC g/dL | O₂ Slope | Slope | Intercept | Unknown Set | SEP g/dL | Bias g/dL |
|---|---|---|---|---|---|---|---|---|
| A | 0.996 | 0.27 | −0.109 | 159.01 | 11.00 | B1 | 0.76 | −0.51 |
|   |   |   |   |   |   | B  | 0.62 | −0.32 |
| B | 0.999 | 0.16 | −0.083 | 147.63 | 9.59 | A1 | 0.49 | 0.28 |
|   |   |   |   |   |   | A  | 0.46 | 0.15 |

TABLE VII

Prediction of Individual Sets Against
Other Individual Sets With Adjustment For
Percent Oxygen Saturation From A Co-Oximeter
For Hematocrit at 1169 nm After
Second Derivative Pre-Processing

| Known Set | R | SEC % | O₂ Slope | Slope | Intercept | Unknown Set | SEP % | Bias % |
|---|---|---|---|---|---|---|---|---|
| A | 0.997 | 0.70 | −0.305 | 459.66 | 31.50 | B1 | 2.97 | −2.01 |
|   |   |   |   |   |   | B  | 2.36 | −1.62 |
| B | 0.983 | 0.69 | −0.253 | 439.55 | 29.64 | A1 | 2.08 | 1.68 |
|   |   |   |   |   |   | A  | 1.78 | 1.38 |

With the use of the complete sets A or B as the known set, a direct comparison was made between the results shown in Tables III and VI and V and VII, respectively. In every instance other than the already acceptable prediction by set A of set B1, use of percent oxygen saturation as a second independent variable provided a higher correlation R, a more precise SEC, a more accurate and precise SEP, and a more accurate bias. Also, the under-prediction reflected in the change in bias between prediction of segregated sets B1 or A1 and full sets B or A was less pronounced.

The greatest adjustment provided by including the percent oxygen saturation as an independent variable occurred with respect to set B, previously seen as extremely marginal in prediction as either the known set or the unknown set. Thus, the percent oxygen saturation contributes more to the accuracy and precision of the prediction when the percent oxygen saturations for the spectra are more varied.

For a known occasion where percent oxygen saturation is lower than 95 percent or for an unknown occasion, use of a linear functional equation including percent oxygen saturation as a second independent variable provided most useful results. FIG. 12 shows the high resolution of accuracy between the method used in this Example 5 and the independent quantification used for the same spectra and how that resolution is more accurate than that shown in FIG. 8.

EXAMPLE 6

The effect of variations in percent oxygen saturation among the spectra was also calculated from the spectra without use of the co-oximeter. The ratio of the wavelengths of 700 and 820 nm, was proportional to the percent oxygen saturation which existed in each sample as it was analyzed. That ratio data from the originally detected spectra replaced one column of transformed spectral data to achieve a multiple variable set of data, which the Near Infrared Spectral Analysis software and the VAX IDL software computed in the manner described in Examples 1–3 to yield the mathematical results. Table VIII shows the results found for hemoglobin when the adjustment for percent oxygen saturation was determined by the ratio described here. Table IX shows the analogous results found for hematocrit.

TABLE VIII

Prediction of Individual Sets Against
Other Individual Sets With Adjustment
For Percent Oxygen Saturation From A Spectral Ratio
For Hemoglobin at 1170 nm After
Second Derivative Pre-Processing

| Known Set | R | SEC g/dL | O₂ Slope | Slope | Intercept | Unknown Set | SEP g/dL | Bias g/dL |
|---|---|---|---|---|---|---|---|---|
| A | 0.997 | 0.259 | 13.07 | 168.9 | −11.33 | B1 | 0.94 | −0.52 |
|   |   |   |   |   |   | B  | 0.73 | −0.46 |
| B | 0.981 | 0.242 | 11.84 | 166.4 | −9.624 | A1 | 0.62 | 0.48 |
|   |   |   |   |   |   | A  | 0.59 | 0.48 |

TABLE IX

Prediction of Individual Sets Against
Other Individual Sets With Adjustment
For Percent Oxygen Saturation From A Spectral Ratio
For Hematocrit at 1169 nm After
Second Derivative Pre-Processing

| Known Set | R | SEC % | O₂ Slope | Slope | Intercept | Unknown Set | SEP % | Bias % |
|---|---|---|---|---|---|---|---|---|
| A | 0.997 | 0.72 | 36.46 | 495.38 | −31.18 | B1 | 3.90 | −2.19 |
|   |   |   |   |   |   | B  | 2.67 | −2.18 |
| B | 0.970 | 0.92 | 36.05 | 496.69 | −28.69 | A1 | 2.72 | 2.22 |
|   |   |   |   |   |   | A  | 2.61 | 2.22 |

A comparison of the results shown in Table VIII with Table VI and shown in Table IX with Table VII found that the use of a ratio of wavelengths from the same spectral data as that used in the prediction found the accuracy and precision of the prediction to be comparable.

EXAMPLES 7–10

RATIO PRE-PROCESSING TECHNIQUE

EXAMPLE 7

The use of a ratio pre-processing technique provided comparable results to the use of the multiple derivative pre-processing technique. Using the same spectra and data as shown in Table I in Example I, the ratio pre-processing method depicted in FIG. 3 was employed using the following Fortran generated software program described herein, with a personal computer, to select the best ratio, to perform the linear regression, and to save the regression coefficients (steps 224, 225, 227, and 228 of FIG. 3). Procedures in the VAX IDL Interactive Data Language software program described in Example 1 were used to perform the ratio pre-processing on the unknown sample, apply the regression model and predict the property, (steps 231, 232, and 233 of FIG. 3) and to compute the SEC, SEP, and bias for validation purposes.

```
Fortran Software Program
(Complies with ANSI Fortran 77)
Copyright, 1989, Minnesota Mining and Manufacturing Company REAL DATA(200,500),YVAL(200),TEMP(1500)
      REAL DOUT(500,500),NSPEC,NWAVE
      CHARACTER*30 FILEN
      WRITE (6, 100)
100   FORMAT (' ENTER THE SPECTRAL DATA FILE NAME: ')
      READ (5, 101) FILEN
101   FORMAT (A)
      OPEN (20, FILE=FILEN, STATUS='OLD',
     1FORM='UNFORMATTED', ERR=9999)
      READ (20) NSPEC, NWAVE
10    WRITE (6,102)
102   FORMAT (' ENTER SPACING BETWEEN SPECTRAL
      POINTS: ')
      READ (5,*) NSKIP
      IF (NWAVE/NSKIP .GT. 500) GOTO 10
      DO 20 I=1,NSPEC
      READ (20) (TEMP(J), J=1, NWAVE)
      DO 20 J=0,NWAVE/NSKIP-1
20    DATA(I,J+1) = TEMP(NSKIP*J+1)
      CLOSE (20)
      WRITE (6, 103)
103   FORMAT (' ENTER THE PROPERTY DATA FILE NAME: ')
      READ (5, 101) FILEN
      OPEN (20, FILE=FILEN, STATUS='OLD',
     1FORM='UNFORMATTED', ERR=9999)
      READ (20) NSPEC
      DO 30 I=1,NSPEC
30    READ (20) YVAL(I)
      CLOSE (20)
      AVEY = YVAL(1)
      DO 40 I=2,NSPEC
40    AVEY = AVEY + YVAL(I)
      AVEY = AVEY / NSPEC
      YFACT = 0.0
      DO 50 I = 1, NSPEC
50    YFACT = YFACT + (YVAL(I)-AVEY)*(YVAL(I)-AVEY)
      IF (YFACT .LT. 1.0E-06) GO TO 9999
      ZCORR = 0.0
      DO 80 I=1,NWAVE/NSKIP
      DO 80 J=1,NWAVE/NSKIP
      AVEX=0.0
      DO 60 K=1,NSPEC
      TEMP(K) = DATA(K,J)/(DATA(K,I)+1.0E-6)
60    AVEX = AVEX + TEMP(K)
      AVEX = AVEX / NSPEC
      XFACT = 0.0
      XYFACT = 0.0
      DO 70 K=1,NSPEC
      XFACT = XFACT + (TEMP(K)-AVEX)*(TEMP(K)-AVEX)
70    XYFACT = XYFACT + (TEMP(K)-AVEX)*(YVAL(K)-AVEY)
      IF (ABS(XFACT) .LT. 1E-6) DOUT(J,I)=0.0
      IF (ABS(XFACT) .GE. 1E-6)
     1DOUT(J,I)=(XYFACT/XFACT)*(XYFACT/YFACT)
      IF (DOUT(J,I) .LE. ZCORR) GO TO 80
      ZCORR = DOUT(J,I)
      ZXCOL = J
      ZYCOL = I
      ZAVEX = AVEX
      ZXFACT = XFACT
      ZXY = XYFACT
80    CONTINUE
      WRITE (6,104) INT(1+(ZXCOL-1)*NSKIP),
     1INT(1+(ZYCOL-1)*NSKIP)
104   FORMAT (/,' NUMERATOR WAVELENGTH: ',I4,
     1/,' DENOMINATOR WAVELENGTH: ',I4)
      SLOPE = ZXY/ZXFACT
      WRITE (6,105) ZCORR, SLOPE, AVEY-SLOPE*ZAVEX
105   FORMAT (/,' CORRELATION COEFF.: ',1PE11.4,
     1/,' SLOPE: ',E10.3,/,' INTERCEPT: ',E10.3)
      WRITE (6,106)
106   FORMAT (' ENTER THE OUTPUT FILE NAME: ')
      READ (5, 101) FILEN
      OPEN (20, FILE=FILEN, FORM='UNFORMATTED',
      STATUS='NEW')
      WRITE (20) NWAVE/NSKIP,NWAVE/NSKIP,0.0,0.0
      DO 90 I=1,NWAVE/NSKIP
```

```
Fortran Software Program
(Complies with ANSI Fortran 77)
Copyright, 1989, Minnesota Mining and Manufacturing Company 90    WRITE (20) (DOUT(J,I), J=1,NWAVE/NSKIP)
9999  CLOSE (20)
      STOP
      END
```

The ratio pre-processing technique computed substantially possible wavelength pairs, as described above, in order to find the best correlation in the area of the water absorbance peak and another absorbance measuring point.

For the analysis of hemoglobin, Sets A and B were combined, comprising 27 spectra. Using the ratio pre-processing technique, the mathematical analysis depicted in FIG. 3 was performed and yielded a pair of wavelengths of 843 and 1173 nm with a multiple correlation coefficient (R) of 0.996 and a standard error of calibration (SEC) of 0.26 g/dL, with a computed slope of 36.818 and an intercept of −37.807. This pair is in the vicinity of the isosbestic point for oxy and deoxy hemoglobin and the broad absorbance peak of water, respectively. However, for purposes of comparison with the examples of ratio pre-processing technique used in U.S. patent application Ser. No. 07/408,746, (File Number 44446USA8A) filed by some of the applicants of this application, the pair of wavelengths of 820 and 1161 nm were chosen, which yielded the nearly similar results of R=0.983, SEC=0.53 g/dL, and a slope of 40.347 and intercept of −40.773.

Figure 7:
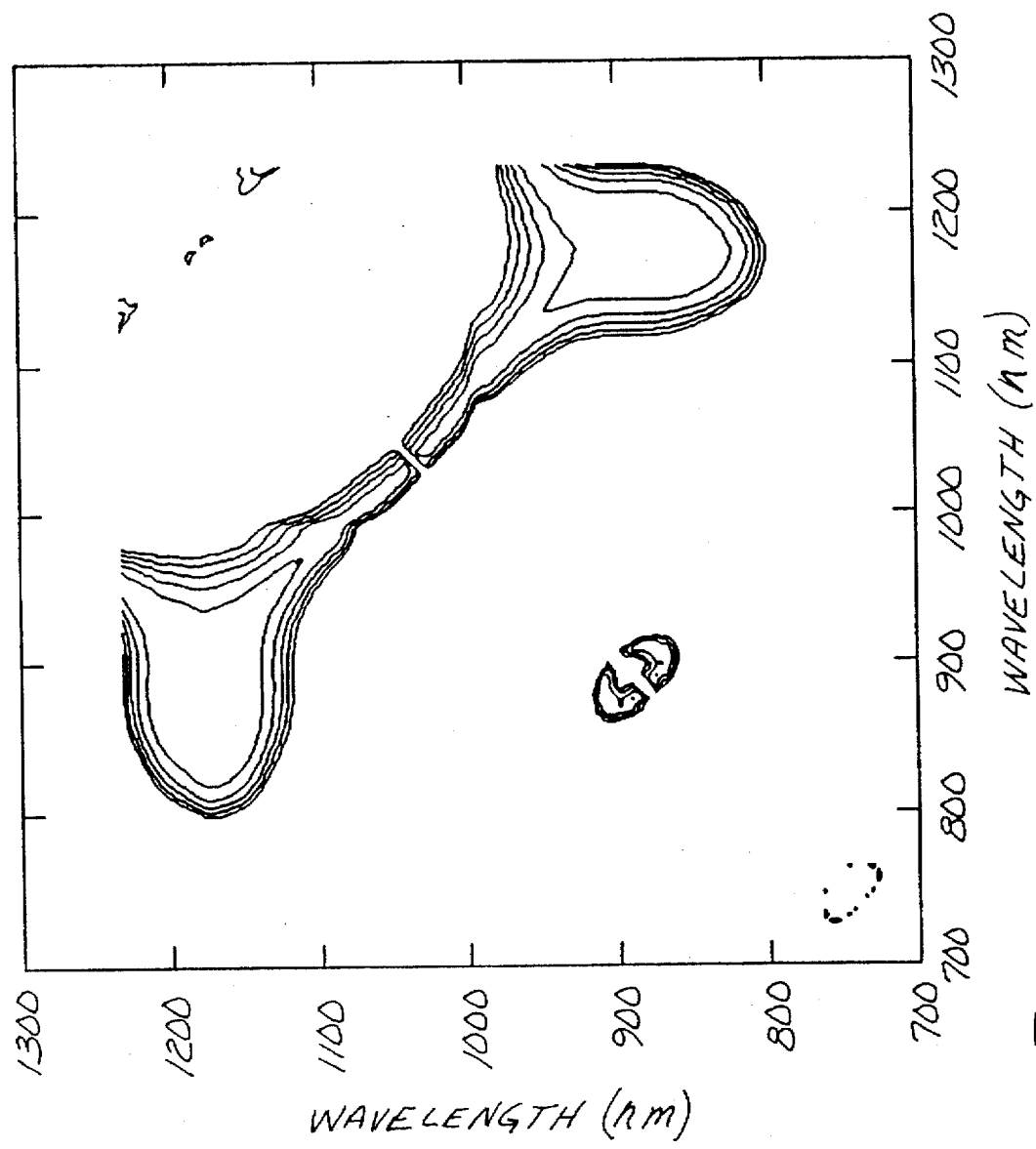
FIG. 7 is a correlation map of correlation cofficient squared versus wavelength for hemoglobin after ratio pre-processing and regression analysis of the spectral data was performed against hemoglobin.

To confirm the selection of the 820/1161 pair of wavelengths, a correlation map was generated, and depicted as FIG. 7 using the VAX IDL, Interactive Data Language software described above.

From that map measuring the lines of equal correlation at 0.875, 0.90, 0.925, 0.95, and 0.975 using the squares of the multiple correlation coefficients, it was found that in the range of 1150 to 1190 nm corresponding to the broad absorbance peak of the water content had a broad plateau. The range of 800 to 850 nm also showed a broad plateau. Pairs of wavelengths within these regions would provide acceptable results.

Thus, in this instance using procedures in the VAX IDL software described above and the ratio of 820 nm to 1161 nm, the linear functional equation using a single independent variable was:

$$\text{Hemoglobin} = -40.773 + 40.347 * (\text{Absorbance}_{820} / \text{Absorbance}_{1161})$$

Table X shows the results found using this equation as applied to predict each set A1, A, B1, and B against the combined set A+B for hemoglobin concentration.

TABLE X

Prediction of Individual Sets Against
Combined Set For Hemoglobin at Ratio of 820/1161 nm

| Set | R | SEC g/dL | Bias g/dL |
|---|---|---|---|
| A1 | 0.998 | 0.32 | −0.16 |
| A | 0.992 | 0.39 | 0.00 |
| B1 | 0.994 | 0.36 | −0.22 |
| B | 0.832 | 0.92 | 0.14 |

A comparison of the results found in Table X with the results found in Table II showed the relatively more precise linear functional correlation using the ratio pre-processing technique. However, among the sets studied in Table X, set B showed the effects on precision of lower percent oxygen saturation spectra creating an imbalance within a set of limited numbers for the training set. With adequate balance of variations in the training set spectra, even if the unknown sample's spectrum were quite abnormal, use of ratio pre-processing technique in the formation of the linear functional correlation would have provided acceptable results for calibration.

The validation of the performance of the selected linear functional equation described in this Example 7 was performed to assess standard error of prediction (SEP) and bias. Each set was used as a known and used to predict each other set as if such other set were unknown. Table XI shows the results found.

TABLE XI

Prediction of Individual Sets Against
Other Individual Sets For Hemoglobin
After Ratio Pre-Processing at 820/1161 nm

| Known Set | R | SEC g/dL | Slope | Intercept | Unknown Set | SEP g/dL | Bias g/dL |
|---|---|---|---|---|---|---|---|
| A1 | 0.998 | 0.20 | 42.817 | −43.793 | B1 | 0.34 | −0.21 |
|  |  |  |  |  | B | 0.99 | 0.18 |
| A | 0.992 | 0.39 | 41.071 | −43.683 | B1 | 0.42 | −0.27 |
|  |  |  |  |  | B | 0.93 | 0.10 |
| B1 | 0.995 | 0.15 | 43.195 | −44.047 | A1 | 0.34 | 0.24 |
|  |  |  |  |  | A | 0.63 | 0.42 |
| B | 0.832 | 0.70 | 26.227 | −23.170 | A1 | 1.63 | −0.99 |
|  |  |  |  |  | A | 1.59 | −0.98 |

The results provide proof of the accuracy and the precision of the linear functional equation for predicting hemoglobin in a dynamic condition of an extracorporeal blood loop of a mammal. Recognizing the effects of outlier spectra in set B as previously described in a smaller set than that to be used in forming the training set, the most precise predictions arise from segregated sets A1 and B1, followed by the predictions of and with set A. The trend in the bias is slightly toward the positive, but all sets were predicting within a range of acceptable bias.

EXAMPLE 8

The same experiments as those described in Example 7 were conducted for the analysis of hematocrit using the ratio pre-processing technique computed using the same software and procedures as described in Example 7. The combined sets A and B were analyzed for the best wavelength pair not likely to be rendered inaccurate by changes in concentration of the various forms of hemoglobin, i.e., in the range of 1150–1190 nm and around the isosbestic point. The combined sets having 27 individual spectra, yielded acceptable results.

As in the case of the hemoglobin of Example 7, the wavelength pair initially selected by the mathematical analysis was around 855 nm and 1161 nm (R=0.993 and SEC= 0.93%) with the former in the region of a broad hemoglobin absorbance peak. Therefore, using a correlation map generated in the same manner as that for Example 7, it was determined that use of the same wavelength pair of 820/1161 nm would provide acceptable results. That wavelength pair yielded the following results: R=0.982 and SEC=1.54%, with a slope of 112.74 and an intercept of −113.62.

The combined set A+B was then used as a known set and the individual sets A1, A, B1, and B were predicted therefrom to assess standard error of calibration. The results are shown in Table IV.

TABLE XII

Predict Individual Sets Against
The Combined Set For Hematocrit After
Ratio Pre-Processing at 820/1161 nm

| Set | R | SEC (%) | Bias (%) |
|---|---|---|---|
| A1 | 0.998 | 0.93 | −0.29 |
| A | 0.991 | 1.25 | 0.15 |
| B1 | 0.987 | 1.94 | −1.25 |
| B | 0.835 | 2.52 | −0.35 |

As seen in Table XII, sets A1 and B1 were more precise than sets A and B. The change in bias from smaller sets A1 and B1 to sets A and B, respectively, was more positive. But all were within acceptable ranges.

The individual sets A1, A, B1, and B were treated as known sets and the other sets were treated as unknown sets to assess standard error of prediction and bias. Table XIII shows the results obtained.

TABLE XIII

Predict Individual Sets Against
Other Individual Sets For Hematocrit
After Ratio Pre-Processing at 820/1161 nm

| Known Set | R | SEC (%) | Slope | Intercept | Unknown Set | SEP (%) | Bias (%) |
|---|---|---|---|---|---|---|---|
| A1 | 0.998 | 0.53 | 122.53 | −126.08 | B1 | 2.32 | −1.57 |
|  |  |  |  |  | B | 2.80 | −0.53 |
| A | 0.991 | 1.18 | 117.50 | −120.02 | B1 | 2.58 | −1.75 |
|  |  |  |  |  | B | 2.87 | −0.78 |
| B1 | 0.987 | 0.68 | 125.02 | −127.60 | A1 | 2.03 | 1.73 |
|  |  |  |  |  | A | 2.82 | 2.29 |
| B | 0.835 | 2.08 | 78.72 | −70.63 | A1 | 3.63 | −1.61 |
|  |  |  |  |  | A | 3.57 | −1.52 |

As seen in comparison with the results shown in Table XI, the same or similar trends were found for hematocrit as found for hemoglobin concentration. Segregated sets A1 and B1 provided the more precise predictions against each other, but the larger sets A and B have acceptable precision. The prediction by set B and the prediction of set B showed the effects that two outlier spectra can have on a smaller set having less robustness of spectra, although the effect is less pronounced using the ratio pre-processing technique compared with the second derivative transformation pre-processing technique.

Bias for the predictions by all of the sets were more negative when predicting the segregated sets A1 or B1 than when predicting the full sets A or B, indicating a possible over-prediction is possible when the spectra has a lower percent oxygen saturation. But the bias in all sets' predictions is acceptable.

Figure 9:
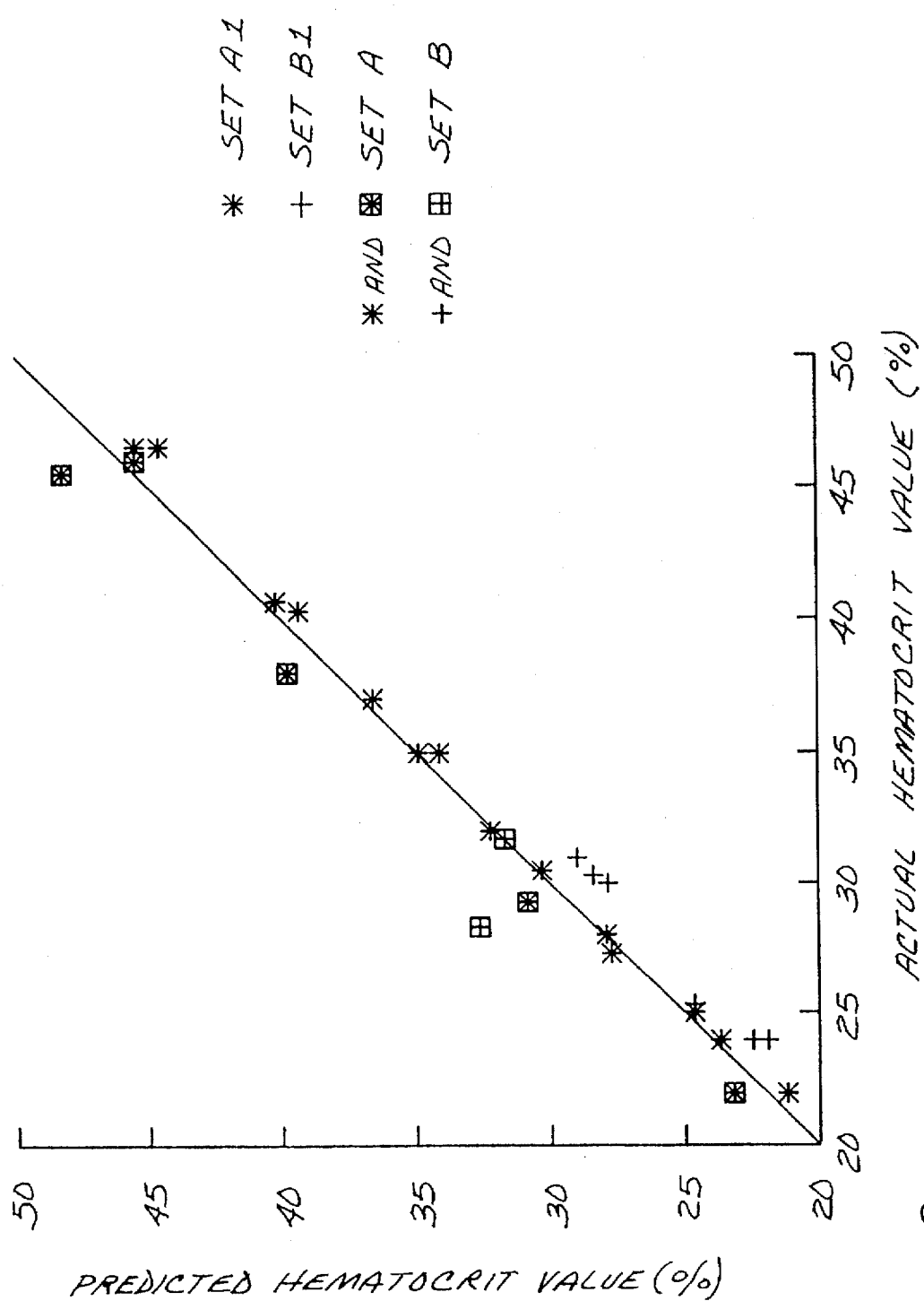
FIG. 9 is a graph showing the accuracy of prediction of hematocrit after ratioing pre-processing compared with actual hematocrit values determined by prior art methods.

FIG. 9 is a graph of the comparison of predictions of set A to the actual independently quantified values for hematocrit.

EXAMPLE 9

As counterpoint to the experiments of Example 5, the use of the percent oxygen saturation was employed as a second independent variable while using the ratio pre-processing technique even though consistently acceptable results were obtained with a single independent variable linear functional equation. FIG. 11 depicts the method of the invention altered to adjust for the use of the second independent variable. The 820/1161 nm ratio computed with the VAX IDL software was added with the co-oximeter measurements to produce a linear summation, and then computed with a multiple linear regression analysis procedure of the VAX IDL software to yield the mathematical results. Tables XIV and XV show the results found when including the co-oximeter measurements of percent oxygen saturation into the equation for hemoglobin and hematocrit, respectively.

TABLE XIV

Prediction of Individual Sets Against
Other Individual Sets With Adjustment
for Percent Oxygen Saturation From A Co-Oximeter
For Hemoglobin After Ratio Pre-Processing at 820/1161 nm

| Known Set | R | SEC g/dL | $O_2$ Slope | Slope | Inter-cept | Un-known Set | SEP g/dL | Bias g/dL |
|---|---|---|---|---|---|---|---|---|
| A | 0.997 | 0.23 | 0.0273 | 41.506 | −44.820 | B1 | 0.33 | −0.15 |
|   |   |   |   |   |   | B  | 0.56 | −0.03 |
| B | 0.945 | 0.46 | 0.0418 | 41.935 | −46.633 | A1 | 0.30 | 0.17 |
|   |   |   |   |   |   | A  | 0.32 | 0.11 |

TABLE XV

Prediction of Individual Sets Against
Other Individual Sets With Adjustment
For Percent Oxygen Saturation From A Co-Oximeter
For Hematocrit After Ratio Pre-Processing at 820/1161 nm

| Known Set | R | SEC % | $O_2$ Slope | Slope | Inter-cept | Un-known Set | SEP % | Bias % |
|---|---|---|---|---|---|---|---|---|
| A | 0.997 | 0.67 | 0.0850 | 118.86 | −129.79 | B1 | 2.55 | −1.38 |
|   |   |   |   |   |   | B  | 2.36 | −1.18 |
| B | 0.928 | 1.58 | 0.1129 | 121.17 | −134.02 | A1 | 1.91 | 1.54 |
|   |   |   |   |   |   | B  | 1.77 | 1.42 |

With the use of the complete sets A and B as the known set, a direct comparison was made between the results shown in Tables XI and XIV and XIII and XV, respectively. In every instance, use of percent oxygen saturation as a second independent variable provided a higher correlation R, a more precise SEC, a more accurate and precise SEP, and a smaller bias, than the already acceptable results using the linear functional equation with the single ratio pair independent variable. While there was less adjustment for set B than found to be necessary in Examples 1–6, there was more adjustment provided by the second independent variable for set B than for the other sets. Thus, the percent oxygen saturation contributes more to the accuracy and precision of the prediction when the percent oxygen saturations for the spectra are more varied.

Figure 13:
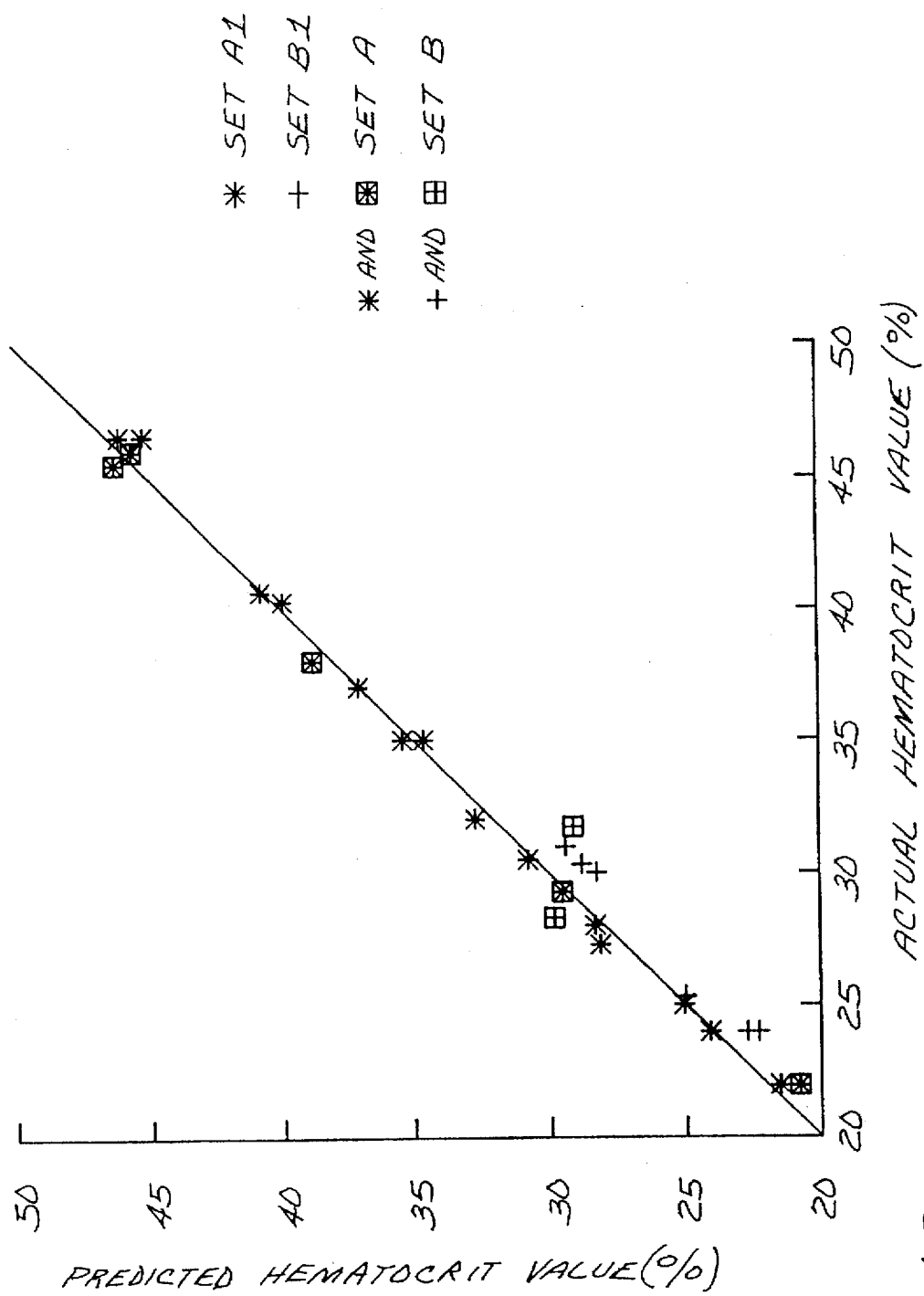
FIG. 13 is a graph showing the accuracy of prediction of hematocrit after ratioing pre-processing and adjusting for the different forms of hemoglobin present in the whole blood, compared with actual hematocrit values determined by prior art methods.

For a known occasion where percent oxygen saturation is lower than 95 percent or for an unknown occasion, use of a linear functional equation including percent oxygen saturation as a second independent variable provided most useful results. FIG. 13 shows the high resolution of accuracy between the method used in this Example 9 and the independent quantification used for the same spectra and how that resolution is more accurate than that shown in FIG. 9.

EXAMPLE 10

The effect of variations in percent oxygen saturation among the spectra was also calculated from the spectra without use of the co-oximeter. The ratio of the absorbances at the wavelengths of 700 and 820 nm was proportional to the percent oxygen saturation existing in each sample as it was analyzed. The 820/1161 nm ratio computed with the VAX IDL software was added with the 700/820 nm ratio to produce a linear summation, and then computed with a multiple linear regression analysis procedure of the VAX IDL software to yield the for hemoglobin when the adjustment for percent oxygen saturation was determined by the ratio described here. Table XVII shows the analogous results found for hematocrit.

TABLE XVI

Prediction of Individual Sets Against
Other Individual Sets With Adjustment
For Percent Oxygen Saturation From A Spectral Ratio
For Hemoglobin After Ratio Pre-Processing at 820/1161 nm

| Known Set | R | SEC % | $O_2$ Slope | Slope | Inter-cept | Un-known Set | SEP % | Bias % |
|---|---|---|---|---|---|---|---|---|
| A | 0.998 | 0.21 | −3.109 | 40.758 | −38.561 | B1 | 0.35 | −0.17 |
|   |   |   |   |   |   | B  | 0.56 | −0.02 |
| B | 0.960 | 0.39 | −5.421 | 40.725 | −36.410 | A1 | 0.36 | 0.24 |
|   |   |   |   |   |   | A  | 0.35 | 0.12 |

TABLE XVII

Prediction of Individual Sets Against
Other Individual Sets With Adjustment
For Percent Oxygen Saturation From A Specral Ratio
For Hematocrit After Ratio Pre-Processing at 820/1161 nm

| Known Set | R | SEC % | $O_2$ Slope | Slope | Inter-Intercept | Un-known Set | SEP % | Bias % |
|---|---|---|---|---|---|---|---|---|
| A | 0.998 | 0.60 | −9.647 | 116.54 | −110.40 | B1 | 2.61 | −1.43 |
|   |   |   |   |   |   | B  | 2.30 | −1.14 |
| B | 0.943 | 1.40 | −14.858 | 118.46 | −106.91 | A1 | 2.18 | 1.77 |
|   |   |   |   |   |   | A  | 1.88 | 1.49 |

A comparison of the results shown in Table XVI with Table XIV and shown in Table XVII with Table XV found that the use of a ratio of wavelengths from the same spectral data as that used in the prediction were quite comparable and acceptable.

Embodiments of the invention have been described using examples. However, it will be recognized that the scope of the invention is not to be limited thereto or thereby.

What is claimed is:

1. A method for analyzing a property of biological matter having a water content in a dynamic condition, the biological matter approximated to comprise a first compartment related to the property to be analyzed and a second compartment having a proportionally larger or smaller amount of water than the first compartment, the method comprising:

(a) observing multiple samples of biological matter in a dynamic condition;

(b) irradiating with near infrared light said multiple samples of the biological matter;

(c) detecting the near infrared absorption spectrum of each of said multiple samples as spectral data consisting of absorbance intensities;

(d) applying a ratio pre-processing technique to the spectral data of absorbance intensities of the spectrum of each of said multiple samples to identify a multiplicity of ratio wavelength pairs;

(e) independently quantifying the property to be analyzed for each of said multiple samples;

(f) establishing a training set from said near infrared absorption spectra of step (d) of said multiple samples using the multiplicity of ratio wavelength pairs; and (g) statistically identifying the nature of a best two compartment mathematical correlation between the property to be analyzed in the first compartment and the water content in the biological matter (1) by correlating values obtained during step (e) with values obtained during step (f) and (2) by selecting a ratio wavelength pair of absorbance intensities in which one wavelength is a strong near infrared wavelength absorbance peak of the water content and in which the second wavelength of the ratio wavelength pair is another near infrared wavelength absorbance measuring point having absorbances in the first compartment which minimize variability in the property to be analyzed.

2. The method according to claim 1, further comprising the steps of:

(h) observing an unknown sample of the biological matter in a dynamic condition;

(i) irradiating said unknown sample with near infrared light;

(j) detecting near infrared spectrum of said unknown sample as spectral data consisting of absorbance intensities;

(k) applying said ratio pre-processing technique using the ratio wavelength pair selected in step (g) to the spectral data of absorbance intensities of said spectrum of said unknown sample; and (l) predicting the property to be analyzed in said unknown sample by utilizing said best two compartment mathematical correlation obtained in said statistically identifying step (g).

3. A method according to claim 2, wherein the biological matter is whole blood and the property of the first compartment to be analyzed is hematocrit.

4. A method according to claim 2, wherein the biological matter is whole blood and the property of the first compartment to be analyzed is the hemoglobin concentration in the whole blood.

5. A method according to claim 2, wherein said detecting step (c) and said detecting step (j) use spectral analysis instrumentation which records said absorbance spectra of said multiple samples and said unknown sample in the dynamic condition of the biological matter flowing through the spectral analysis instrumentation.

6. A method according to claim 5, wherein detecting step (c) and said detecting step (j) use transmittance detection components in said spectral analysis instrumentation.

7. A method according to claim 5, wherein detecting step (c) and said detecting step (j) use reflectance detection components in said spectral analysis instrumentation.

8. A method according to claim 2, wherein said multiple samples are of at least one known organism of a given biological species; and wherein said unknown sample is of the same biological species as said multiple samples.

9. A method according to claim 1, wherein said statistically identifying step (g) uses linear regression analysis.

10. A method according to claim 1, wherein said statistically identifying step (g) uses multiple linear regression analysis.

11. A method according to claim 1, wherein said statistically identifying step (g) uses stepwise regression analysis.

12. A method according to claim 1, wherein said statistically identifying step (g) uses partial least squares regression analysis.

13. A method according to claim 1, wherein said mathematical correlation in said statistically identifying step (g) comprises a linear function related to a near infrared absorbance peak of water in the absorbance spectra of said multiple samples subjected to said pre-processing technique.

14. A method according to claim 13, wherein the biological matter is whole blood and said absorbance peak of water occurs in the near infrared spectra from about 1150 to about 1190 nanometers.

15. A method according to claim 13, wherein the biological matter is whole blood, said absorbance peak of water occurs in the near infrared spectra from about 1150 to about 1190 nanometers, and said another near infrared wavelength absorbance measuring point is the isosbestic point of oxyhemoglobin and deoxyhemoglobin.

16. A method according to claim 2, wherein said mathematical correlation in said statistically identifying step (g) comprises a linear function related to a near infrared absorbance peak of water in the absorbance spectra of said multiple samples subjected to said pre-processing technique.

17. A method according to claim 16, wherein the biological matter is whole blood and said absorbance peak of water occurs in the near infrared spectra from about 1150 to about 1190 nanometers.

18. A method according to claim 16, wherein the biological matter is whole blood, said absorbance peak of water occurs in the near infrared spectra from about 1150 to about 1190 nanometers, and said another near infrared wavelength absorbance measuring point is the isosbestic point of oxyhemoglobin and deoxyhemoglobin.

19. A method according to claim 18, wherein the property to be analyzed is hematocrit and said mathematical correlation solves the equation:

$$Y=b+m*(\text{Absorbance at Isosbestic Point}/\text{Absorbance at said Absorbance Peak of Water})$$

where Y is the value of hematocrit, b ranges from about −70 to about −128, and m ranges from about 78 to about 126.

20. A method according to claim 18, wherein the property to be analyzed is hemoglobin concentration and said mathematical correlation solves the equation:

$$Y=b+m*(\text{Absorbance at Isosbestic Point}/\text{Absorbance at said Absorbance Peak of Water})$$

where Y is the hemoglobin concentration, b ranges from about −23 to about −45, and m ranges from about 26 to about 44.

21. A method according to claim 1, wherein the biological matter is whole blood and the property of the first compartment to be analyzed is hematocrit.

22. A method according to claim 1, wherein the biological matter is whole blood and the property of the first compartment to be analyzed is the hemoglobin concentration in the whole blood.

23. A method according to claim 1, wherein said mathematical correlation statistically identified in step (g) indicates a complementary relationship between the property to be analyzed and the water content.

24. A method according to claim 1, further comprising the steps of:

(1) observing additional samples of biological matter in a dynamic condition;

(2) independently quantifying the property to be analyzed for each of said additional samples;

(3) performing steps (b), (c), and (d) with respect to said additional samples;

(4) predicting the property to be analyzed in said additional samples by utilizing said mathematical correlation obtained in said statistically identifying step (g); and (5) validating said mathematical correlation by comparing the property predicted in step (4) to the property independently quantified in step (2).

25. A method according to claim 24, wherein said validating step (5) employs manual interpretation of the spectra of said additional samples compared to the training set.

26. A method according to claim 25, wherein said validating step (5) employs a statistical method to compare the property predicted in step (4) to the property independently quantified in step (2).

27. A method for analyzing a property of whole animal blood having a water content, the whole animal blood comprising a first compartment related to the property to be analyzed and a second compartment having a proportionally larger or smaller amount of water than the first compartment, the method comprising:

(a) irradiating with near infrared light multiple samples of the whole animal blood;

(b) detecting the near infrared spectrum of each of said multiple samples as spectral data consisting of absorbance intensities;

(c) applying a pre-processing technique to the spectral data of absorbance intensities of the spectrum of each of said multiple samples;

(d) independently quantifying the property to be analyzed for each of said multiple samples;

(e) independently quantifying a value proportional to the percentage oxygen saturation in the whole animal blood for each of said multiple samples;

(f) establishing a training set from said near infrared spectra of step (c) of said multiple samples using processed spectral data comprising a near infrared wavelength absorbance peak of the water content; and (g) statistically identifying the nature of a best two compartment mathematical correlation between the property to be analyzed in the first compartment and the water content in the whole animal blood (1) by correlating values obtained during step (d) and step (e) with values obtained during step (f) and (2) by selecting at least a wavelength absorbance intensity that is a near infrared wavelength absorbance peak of the water content.

28. The method according to claim 27, further comprising the steps of:

(h) irradiating an unknown sample of whole animal blood with near infrared light;

(i) detecting near infrared spectrum of said unknown sample as spectral data consisting of absorbance intensities;

(j) applying said pre-processing technique using each wavelength selected in step (g) to the spectral data of absorbance intensities of said spectrum of said unknown sample;

(k) determining a value proportional to the percent oxygen saturation of the unknown sample; and (l) predicting the property to be analyzed in said unknown sample by utilizing said best two compartment mathematical correlation obtained in said statistically identifying step (g).

29. A method according to claim 28, wherein the property of the first compartment to be analyzed is hematocrit.

30. A method according to claim 28, wherein the property of the first compartment to be analyzed is the hemoglobin concentration in the whole blood.

31. A method according to claim 28, wherein said detecting step (b) and said detecting step (i) use spectral analysis instrumentation which records said absorbance spectra of said multiple samples and said unknown sample in the dynamic condition of the whole animal blood flowing through the spectral analysis instrumentation.

32. A method according to claim 31, wherein detecting step (b) and said detecting step (i) use transmittance detection components in said spectral analysis instrumentation.

33. A method according to claim 31, wherein detecting step (b) and said detecting step (i) use reflectance detection components in said spectral analysis instrumentation.

34. A method according to claim 28, wherein said multiple samples are of at least one known organism of a given biological species; and wherein said unknown sample is of the same biological species as said multiple samples.

35. A method according to claim 28, wherein said determining step (k) comprises using a pulse oximeter to measure the percent oxygen saturation of the unknown sample.

36. A method according to claim 28, wherein said determining step (k) comprises using a co-oximeter to measure the percent oxygen saturation of the unknown sample.

37. A method according to claim 28, wherein said determining step (k) comprises using the ratio of the absorbances of two wavelengths where the ratio of extinction coefficients for oxyhemoglobin and deoxyhemoglobin at one wavelength is different than that ratio at the second wavelength.

38. A method according to claim 37, wherein said absorbance of deoxyhemoglobin is in the range from about 680 nm to about 720 nm and wherein said absorbance of the combination of oxyhemoglobin and deoxyhemoglobin is in the range of about 780 nm to about 830 nm.

39. A method according to claim 38, wherein said validating step (6) employs a statistical method to compare the property predicted in step (5) to the property independently quantified in step (2).

40. A method according to claim 27, wherein said statistically identifying step (g) uses multiple linear regression analysis.

41. A method according to claim 40, wherein said statistically identifying step (g) uses the independently quantified percent oxygen saturation in said multiple samples as a regression variable in said multiple linear regression analysis to determine said mathematical correlation.

42. A method according to claim 40, wherein said statistically identifying step (g) uses multiple stepwise regression analysis with the independently quantified percent oxygen saturation in said multiple samples as a regression variable to determine said mathematical correlation.

43. A method according to claim 40, wherein said statistically identifying step (g) uses partial least squares regression analysis with the independently quantified percent oxygen saturation in said multiple samples as a regression variable to determine said mathematical correlation.

44. A method according to claim 27, wherein said mathematical correlation in said statistically identifying step (g) comprises a linear function related to a near infrared absorbance peak of water in the absorbance spectra of said multiple samples subjected to said pre-processing technique and the percent oxygen saturation in said multiple samples.

45. A method according to claim 28, wherein said mathematical correlation in said statistically identifying step (g)

comprises a linear function related to a near infrared absorbance peak of water in the absorbance spectra of said multiple samples subjected to said pre-processing technique and the percent oxygen saturation in said multiples samples.

46. A method according to claim 45, wherein said pre-processing technique comprises transforming said spectra of said multiple samples of said training set by computing a multiple derivative of said multiple samples.

47. A method according to claim 46, wherein said multiple derivative is the second derivative.

48. A method according to claim 46, wherein said absorbance peak of water occurs in the near infrared spectra from about 1150 to about 1190 nanometers.

49. A method according to claim 48, wherein the property to be analyzed is hematocrit and said mathematical correlation solves the equation:

$$C = B_0 + B_1(A_1) + B_2(A_2)$$

where C is the Hematocrit; $B_0$ ranges from about −31 to about 32; where $A_1$ is a value proportional to the percent oxygen saturation and $B_1$ is the regression coefficient for the percent oxygen saturation and ranges from about −0.4 to about 36; where $A_2$ is the second derivative transformation of said absorbance peak of water and ranges from about 1160 to about 1175 nm and $B_2$ is the regression coefficient of the second derivative transformation of said absorbance peak of water and ranges from about 439 to about 496.

50. A method according to claim 48, wherein the property to be analyzed is concentration of hemoglobin and said mathematical correlation solves the equation:

$$C = B_0 + B_1(A_1) + B_2(A_2)$$

where C is the concentration of hemoglobin; $B_0$ ranges from about −11 to about 11; where $A_1$ is a value proportional to the percent oxygen saturation and $B_1$ is the regression coefficient for the percent oxygen saturation and ranges from about −0.08 to about 13; where $A_2$ is the second derivative transformation of said absorbance peak of water and ranges from about 1160 to about 1175 nm and $B_2$ is the regression coefficient of the second derivative transformation of said absorbance peak of water and ranges from about 147 to about 169.

51. The method according to claim 45, wherein said pre-processing technique comprises applying a ratio consisting of absorbance intensities of a near infrared absorbance peak of the water content in said training set to another near infrared wavelength absorbance measuring point in said source spectra set to obtain a multiplicity of ratio wavelength pairs, wherein said training set is established using the multiplicity of wavelength pairs, wherein the selecting of step (g) comprises selecting a ratio wavelength pair consisting of absorbance intensities in which one wavelength is a near infrared wavelength absorbance peak of the water content and in which the second wavelength of the ratio wavelength pair is another near infrared wavelength absorbance measuring point, and wherein step j applies a ratio pre-processing technique using the ratio wavelength pair selected in step (g).

52. A method according to claim 51, wherein said absorbance peak of water occurs in the near infrared spectra from about 1150 to about 1190 nanometers, and said another near infrared wavelength absorbance measuring point is the isosbestic point of oxyhemoglobin and deoxyhemoglobin.

53. A method according to claim 52, wherein the property to be analyzed is hematocrit and said mathematical correlation solves the equation:

$$C = B_0 + B_1(A_1) + B_2(A_2)$$

where C is the Hematocrit; $B_0$ ranges from about −106 to about −134; where $A_1$ is a value proportional to the percent oxygen saturation and $B_1$ is the regression coefficient for the percent oxygen saturation and ranges from about −15 to about 0.1; where $A_2$ is the ratio of the Absorbance at said Isosbestic Point to the Absorbance at said Absorbance Peak of Water and $B_2$ is the regression coefficient of said absorbance peak of water and ranges from about 116 to about 121.

54. A method according to claim 52, wherein the property to be analyzed is hemoglobin concentration and said mathematical correlation solves the equation:

$$C = B_0 + B_1(A_1) + B_2(A_2)$$

where C is the concentration of hemoglobin; $B_0$ ranges from about −46 to about −36; where $A_1$ is a value proportional to the percent oxygen saturation and $B_1$ is the regression coefficient for the percent oxygen saturation and ranges from about −5 to about 0.02; where $A_2$ is the ratio of the Absorbance at said Isosbestic Point to the Absorbance at said Absorbance Peak of Water and $B_2$ is the regression coefficient of said absorbance peak of water and ranges from about 40 to about 42.

55. A method according to claim 45, wherein said absorbance peak of water occurs in the near infrared spectra from about 1150 to about 1190 nanometers.

56. A method according to claim 44, wherein said pre-processing technique comprises transforming said spectra of said multiple samples of said training set by computing a multiple derivative of said multiple samples.

57. A method according to claim 56, wherein said multiple derivative is the second derivative.

58. A method according to claim 56, wherein said absorbance peak of water occurs in the near infrared spectra from about 1150 to about 1190 nanometers.

59. The method according to claim 44, wherein said pre-processing technique comprises applying a ratio consisting of absorbance intensities of a near infrared absorbance peak of the water content in said training set to another near infrared wavelength absorbance measuring point in said source spectra set to obtain a multiplicity of ratio wavelength pairs, wherein said training set is established using the multiplicity of wavelength pairs, and wherein the selecting of step (g) comprises selecting a ratio wavelength pair consisting of absorbance intensities in which one wavelength is a near infrared wavelength absorbance peak of the water content and in which the second wavelength of the ratio wavelength pair is another near infrared wavelength absorbance measuring point.

60. A method according to claim 59, wherein said absorbance peak of water occurs in the near infrared spectra from about 1150 to about 1190 nanometers, and said another near infrared wavelength absorbance measuring point is the isosbestic point of oxyhemoglobin and deoxyhemoglobin.

61. A method according to claim 44, wherein said absorbance peak of water occurs in the near infrared spectra from about 1150 to about 1190 nanometers.

62. A method according to claim 27, wherein the property of the first compartment to be analyzed is hematocrit.

63. A method according to claim 27, wherein the property of the first compartment to be analyzed is the hemoglobin concentration in the whole blood.

64. A method according to claim 27, wherein said mathematical correlation statistically identified in step (g) indicates a complementary relationship between the property to be analyzed and the water content.

65. A method according to claim 27, wherein said multiple samples are of at least one known organism of a given biological species.

66. A method according to claim 27, further comprising the steps of:
   (1) observing additional samples of biological matter in a dynamic condition;
   (2) independently quantifying the property to be analyzed for each of said additional samples;
   (3) independently quantifying a value proportional to the percentage oxygen saturation in the whole animal blood for each of said additional samples;
   (4) performing steps (a), (b), and (c) with respect to said additional samples;
   (5) predicting the property to be analyzed in said additional samples by utilizing said mathematical correlation obtained in said statistically identifying step (g); and
   (6) validating said mathematical correlation by comparing the property predicted in step (5) to the property independently quantified in step (2).

67. A method of monitoring a property of interest in whole blood of a live patient, nearly simultaneously with flow of the whole blood in the patient, the whole blood approximated to comprise a first compartment related to the property of interest and a second compartment having a proportionally larger or smaller mount of water, comprising:
   (a) establishing a blood flow loop having a diversion section departing from the patient terminating at a flow cell, a return section returning to the patient beginning at a flow cell, and a bypass section between the diversion section and the return section;
   (b) flowing the whole blood through the blood loop;
   (c) using near infrared detecting means to monitor the property of interest in the whole blood flowing through the blood loop;
   (d) identifying the value of the property of interest using a method of correlation of a linear functional relationship;

wherein said linear functional relationship is established by:
   (1) observing multiple samples of whole blood in a dynamic condition;
   (2) irradiating with near infrared light said multiple samples of the whole blood;
   (3) detecting the near infrared adsorption spectrum of each of said multiple samples as spectral data consisting of absorbance intensifies;
   (4) applying a ratio pre-processing technique to the spectral data of absorbance intensities of the spectrum of each of said multiple samples to identify a multiplicity of ratio wavelength pairs;
   (5) independently quantifying the property of interest for each of said multiple samples;
   (6) establishing a training set from said near infrared adsorption spectra of step (4) of said multiple samples using the multiplicity of ratio wavelength pairs; and
   (7) statistically identifying the nature of a best two compartment mathematical correlation between the property to be analyzed in the first compartment and the water content in he whole blood (i) by correlating values obtained during step (5) with values obtained during step (6) and (ii) by selecting a ratio wavelength pair of absorbance intensities in which one wavelength is a strong near infrared wavelength absorbance peak of the water content and in which the second wavelength of the ratio wavelength pair is another near infrared wavelength absorbance measuring point having absorbances in the first compartment which minimize variability in the property of interest.

68. A method according to claim 67, wherein said identifying step (d) comprises determining the property of interest in the whole blood flowing through the blood by applying said mathematical correlation to a near infrared spectrum of the whole blood flowing in the blood loop.

69. A method according to claim 67, wherein the property of interest is hematocrit.

70. A method according to claim 67, wherein the property of interest is hemoglobin.

* * * * *